(12) United States Patent
Gamez-Garcia et al.

(10) Patent No.: US 8,663,612 B2
(45) Date of Patent: Mar. 4, 2014

(54) AMPHOLYTIC TER-POLYMERS FOR USE IN PERSONAL CARE COMPOSITIONS

(75) Inventors: Manuel Gamez-Garcia, New City, NY (US); Xian-Zhi Zhou, Leonia, NJ (US)

(73) Assignee: BASF SE, Ludwigshafen (DE)

( * ) Notice: Subject to any disclaimer, the term of this patent is extended or adjusted under 35 U.S.C. 154(b) by 416 days.

(21) Appl. No.: 12/711,589

(22) Filed: Feb. 24, 2010

(65) Prior Publication Data

US 2010/0226868 A1    Sep. 9, 2010

Related U.S. Application Data

(60) Provisional application No. 61/209,293, filed on Mar. 5, 2009, provisional application No. 61/300,658, filed on Feb. 2, 2010.

(51) Int. Cl.
*A61Q 3/00* (2006.01)
*A61Q 5/02* (2006.01)
*A61Q 5/12* (2006.01)
*A61Q 19/10* (2006.01)

(52) U.S. Cl.
USPC ............. 424/70.11; 424/61; 424/70.122; 424/70.22; 424/401; 524/555; 524/556; 524/597

(58) Field of Classification Search
None
See application file for complete search history.

(56) References Cited

U.S. PATENT DOCUMENTS

| | | | |
|---|---|---|---|
| 4,582,376 A | 4/1986 | Olsson | |
| 4,814,101 A | 3/1989 | Schieferstein et al. | |
| 5,296,218 A | 3/1994 | Chen et al. | |
| 5,302,322 A | 4/1994 | Birtwistle | |
| 5,543,074 A | 8/1996 | Hague et al. | |
| 5,573,709 A | 11/1996 | Wells | |
| 5,575,873 A | 11/1996 | Pieper et al. | |
| 5,609,862 A * | 3/1997 | Chen et al. ................. | 424/70.11 |
| 5,879,670 A | 3/1999 | Melby et al. | |
| 5,977,038 A | 11/1999 | Birtwistle et al. | |
| 6,066,315 A | 5/2000 | Melby et al. | |
| 6,110,451 A | 8/2000 | Matz et al. | |
| 6,200,554 B1 | 3/2001 | Yeoh et al. | |
| 6,348,188 B1 | 2/2002 | Eccleson et al. | |
| 6,361,768 B1 * | 3/2002 | Galleguillos et al. ...... | 424/70.12 |
| 6,451,298 B1 | 9/2002 | Decoster et al. | |
| 6,482,776 B1 | 11/2002 | Matz et al. | |
| 6,511,671 B1 | 1/2003 | Dubief et al. | |
| 6,555,101 B1 | 4/2003 | Kahre et al. | |
| 6,696,053 B1 | 2/2004 | Ma et al. | |
| 6,706,258 B1 | 3/2004 | Gallagher et al. | |
| 6,858,202 B2 | 2/2005 | Niemiec et al. | |
| 6,908,889 B2 | 6/2005 | Niemiec et al. | |
| 7,303,744 B2 | 12/2007 | Wells et al. | |
| 2003/0086894 A1 | 5/2003 | Hensen et al. | |
| 2003/0131424 A1 | 7/2003 | Audousset | |
| 2005/0002871 A1 | 1/2005 | Ivanova et al. | |
| 2005/0202984 A1 | 9/2005 | Schwartz et al. | |
| 2005/0276778 A1 | 12/2005 | Chen et al. | |
| 2006/0123564 A1 | 6/2006 | Nishizawa et al. | |
| 2006/0149013 A1 | 7/2006 | Becker et al. | |
| 2006/0199756 A1 | 9/2006 | Creamer et al. | |
| 2007/0287815 A1 | 12/2007 | Gaillard et al. | |
| 2008/0033129 A1 | 2/2008 | Schechtman et al. | |
| 2008/0057016 A1 | 3/2008 | Geary et al. | |
| 2008/0206355 A1 | 8/2008 | Schwartz et al. | |
| 2010/0105592 A1 | 4/2010 | Yoda et al. | |
| 2011/0009552 A1 | 1/2011 | Criniere et al. | |

FOREIGN PATENT DOCUMENTS

| | | |
|---|---|---|
| CA | 2139495 | 1/1994 |
| EP | 0158531 | 10/1985 |
| EP | 1137397 | 10/1985 |
| EP | 0464993 | 1/1992 |
| EP | 0529833 | 3/1993 |
| EP | 0529883 | 3/1993 |
| EP | 1911778 | 4/2008 |

* cited by examiner

*Primary Examiner* — Jyothsna Venkat
(74) *Attorney, Agent, or Firm* — Shiela A. Loggins

(57) ABSTRACT

Novel ampholytic ter-polymers comprising at least an ethylenically unsaturated cationic monomer, a monomer containing a carboxylic acid or sulfonic acid group and diallyamine or derivative are claimed. Further, the ter-polymers may be used in personal care or personal washing compositions optionally in the presence of conditioning agents such as silicone, fatty amines, fatty amine oxides and fatty quaternaries and/or various benefit agents. The ter-polymer compositions are especially useful in the treatment of keratin-containing substrates. Keratin substrates include, but are not limited to, animal and human hair, skin and nails.

22 Claims, No Drawings

AMPHOLYTIC TER-POLYMERS FOR USE IN PERSONAL CARE COMPOSITIONS

This application claims the benefit of Provisional Application Nos. 61/209,293, filed Mar. 5, 2009 and 61/300,658, filed Feb. 2, 2010 herein both incorporated entirely by reference.

BACKGROUND OF THE INVENTION

1. Field of the Invention

The present invention relates to novel ampholytic ter-polymers, personal care compositions containing said ter-polymers and methods for using such ter-polymers. The herein described ampholytic ter-polymers comprise at least an ethylenically unsaturated cationic monomer, a monomer containing a carboxylic acid or sulfonic acid group and a diallyamine or diallyamine derivative. The ter-polymers and ter-polymer compositions of the present invention are useful in the treatment of keratin-containing substrates. Keratin substrates include, but are not limited to, animal and human hair, skin and nails.

Hair is composed of keratin, a sulfur-containing fibrous protein. The isoelectric point of keratin, and more specifically of hair, is generally in the pH range of 3.2-4.0. Therefore, at the pH of a typical shampoo, hair carries a net negative charge. Consequently, cationic polymers have long been used as conditioners in shampoo formulations, or as a separate conditioning treatment to improve the wet and dry combability of the hair. The substantivity of the cationic polymers for negatively charged hair along with film formation facilitates detangling during wet hair combing and a reduction in static flyaway during dry hair combing. Cationic polymers generally also impart softness and suppleness to hair.

Although cationic polymers and amphoteric polymers have long been used as conditioners in personal care compositions such as shampoos and bodywashes, the commercially available polymers are deficient in providing a certain combination of effects on keratinic substrates. For instance, a certain number of claims related to cationic and amphoteric polymers described in the literature focus, either on a limited number of attributes for the conditioning process such as friction reduction and softness, or on the ability of the polymers to act as deposition aids for silicone only. These type of polymers are disclosed in U.S. Pat. Nos. 5,573,709, 5,977,038, 6,200,554, 6,451,298, 5,302,322, 6,348,188 B1, EP 0 529 883 B1, and U.S. Application Publication Nos. 2006/0123564 and 2005/0002871 herein incorporated entirely by reference.

The shortcomings in the performance of current commercial conditioning polymers have prompted the search for new polymeric materials that will make possible the achievement of a true "2 in 1" conditioning shampoo. Thus, in the area of hair and skin care in particular, there is a need for cationic polymers that will display simultaneously the following characteristics: 1) They should be able to act as deposition aids not only for silicone but also for a wide range of other conditioning actives on keratinic substrates, 2) The polymers should be able to provide by themselves basic conditioning effects to keratinic substrates without the need of any additional conditioning ingredient, and 3) They should be capable of interacting with other conditioning actives to provide conditioning synergies leading to additional and novel conditioning functionalities, i.e. refatting of hair/skin, elimination of hair "squeakiness" after washing, reduced irritation, improved emolliency, softness, wet and dry friction reduction and shine.

The achievement of these three effects with one single cationic polymer poses, however, major technical challenges. This is especially true in "2 in 1" washing or cleansing compositions where the processes of cleansing and deposition are antagonistic in nature; i.e. the cleansing process not only will tend to remove the polymer from the keratinic substrate but also any other conditioner material that deposits on its surface.

The present inventors have successfully designed amphoteric ter-polymers that are able to perform the three tasks described above without affecting the washing process. While not wishing to be bound by theory, it is believed each monomer unit in the ter-polymer backbone has a specific functionality. For instance, the cationic moieties in the ter-polymer are substantive to negative keratinic substrates from the washing compositions, and in addition allow complexation with anionic surfactants. Furthermore, complexation of the ter-polymer with other conditioning materials such as fatty amines and cationic surfactants is achieved by the presence of an anionic monomer unit. Finally, a certain degree of hydrophobicity and polarity for conditioning and moisturization is attained with a third monomer unit formed from diallyamine or derivatives of diallyamine.

With the above described monomer composition the ter-polymer can also form in situ coacervate complexes with the washing composition. These complexes have the appropriate rheology to deposit lubricious layers of ter-polymer/surfactant that aid in the deposition of conditioning actives by flocculation. With these characteristics, when the ampholytic ter-polymers are formulated into washing and rinse-off compositions they have the following properties: 1) The ampholytic ter-polymers of the invention have a strong affinity for keratin substrates even in the presence of anionic surfactants, 2) By being slightly hydrophobic and polar they can provide conditioning on their own, 3) Because of their ability to form simultaneously complexes with anionic, fatty amines, and cationic surfactants they can provide enhanced and added functionalities. For instance, as the ter-polymers are able to deposit layers of polymer/fatty moieties on the keratinic substrates they can also act as refatting agents reducing the effect of "hair squeakiness" characteristic of shampooed hair. This later feature is mostly absent in all polymers used in personal care described so far in the literature.

The use of the ter-polymer in cleansing or washing compositions solves, the precipitation difficulties often encountered when cationic surfactants are added to formulations containing anionic surfactants. 4) Finally, because of their ability to form complex coacervates, the ter-polymers can also act as deposition aids for silicone and other oils when combined with them. Thus, not only do the polymers work effectively as conditioners by themselves on keratinic substrates but also they function as deposition agents for fatty amines, fatty quaternaries, silicone, and other conditioning oils from cleansing and rinse-off compositions providing lubricity, softness, styling manageability, and an overall conditioning synergy to keratinic substrates.

2. Brief Description of the Background Art

Cationic and ampholytic conditioning polymers are known for use in personal care compositions.

Cationic homopolymers are specifically known to have thickening effects on formulations and also to be good as conditioning agents for hair and skin. For example, SAL-CARE SC 96 is a homopolymer of methacryloylethyl trimethylammonium chloride available from Ciba Corporation, Tarrytown, N.Y. It is a well known as a thickener in personal care compositions.

U.S. Publication Application Nos. 2008/0057016, 2008/0206355, 2005/202984 and U.S. Pat. No. 7,303,744 teach homopolymers of acrylamidopropyltrimethyl ammonium chloride (APTAC) and methacrylamidopropyltrimethyl ammonium chloride (MAPTAC) for use in shampoo formulations.

Cationic copolymers such as SALCARE SC60 (APTAC/acrylamide copolymer) available from Ciba Corporation, Tarrytown, N.Y., are taught for use on hair. For example, U.S. Pat. Nos. 5,543,074, 6,908,889, 6,858,202, 6,696,053 and European Application No. 1 911 778 teach copolymers of cationic monomers and acrylamide in hair formulations.

Amphoteric copolymers are also well known for use on hair. For example, U.S. Pat. Nos. 6,555,101, 6,82,776, 6,511,671, 4,814,101, 6,066,315, 6,110,451, and 5,879,670 teach APTAC-acrylic acid copolymers for use in hair. Several U.S. Published Application Nos. teaching similar copolymers are 2005/0276778, 2003/0086894, 2003/0131424 and 2008/0033129 and Canadian Application No. 2139495. Also cationic celluloses such quaternized hydroxethyl cellulose and cationic guar gum are well known for use in hair.

Further, U.S. Pat. No. 6,348,188 B1, U.S. Pat. No. 6,706,258 B1, and European Application Nos. EP 0 529 883 B1, EP 1 137 397 B1 and EP 0 158 531 B1 teach various cationic polymers capable of depositing silicone on hair.

However, none of these patents or publications teach the inventive amphoteric ter-polymer described herein nor do the above described cationics or amphoterics show the multiple advantages of the present amphoteric ter-polymer. The inventive ter-polymers offer a wider range of conditioning benefits to hair and skin than those previously described in the known art. The ter-polymers are especially useful in 2-in-1 shampoos.

SUMMARY OF THE INVENTION

The present invention embodies novel conditioning polymers.

A conditioning polymer formed from
i.) a cationic monomer defined by formula (I)

$$R_1 - \underset{H}{\overset{R_2}{C}} = \underset{O}{\overset{R_3}{C}} - X - L - \overset{R_4}{\underset{R_5}{N^+}} \quad A^- \qquad (I)$$

in which:
$R_1$ and $R_2$ are independently hydrogen or methyl,
$R_3$, $R_4$ and $R_5$ are independently linear or branched $C_1$-$C_{30}$ alkyl radicals,
X is NH, $NR_6$ or oxygen,
$R_6$ is $C_1$-$C_6$ alkyl,
L is $C_nN_{2n}$,
n is an integer from 1 to 5,
and A– is an anion derived from an organic or inorganic acid, such as a methosulphate anion or halide, such as chloride or bromide;
  ii.) at least one anionic monomer selected from the group consisting of ethylenically unsaturated carboxylic acid and sulfonic acid containing monomers;
and
  iii.) a diallyl amine monomer defined by formulae (II) or (III)

$$\underset{R_7 \quad R_9 \quad R_8}{\diagup\!\!\!\diagdown N \diagdown\!\!\!\diagup} \qquad (II)$$

$$\underset{R_7 \quad R_9 \quad R_8}{\diagup\!\!\!\diagdown \overset{R_{10}}{N^+} \diagdown\!\!\!\diagup} \qquad (III)$$

in which,
$R_7$ and $R_8$ are independently hydrogen or $C_1$-$C_4$ alkyl,
$R_9$ is hydrogen, branched or linear $C_1$-$C_{30}$ alkyl, $C_1$-$C_{30}$ alkoxy, $$* \!-\! \{AO\}_m \!-\! R_{11},$$

hydroxy substituted $C_1$-$C_{10}$ alkyl, $C_7$-$C_9$ alkylphenyl, carboxyalkyl, alkoxyalkyl and carboxyamidalkyl,
$R_{10}$ is hydrogen, $C_1$-$C_{20}$ alkyl, $C_5$-$C_{10}$ cycloalkyl or an unsubstituted or substituted benzyl radical,
with the proviso that if $R_{10}$ is other than hydrogen, then $R_9$ is $$* \!-\! \{AO\}_m \!-\! R_{11},$$

AO is a $C_1$-$C_{12}$ alkylene oxide or mixtures of two or more types of $C_1$-$C_{12}$ alkylene oxides, it being possible for the two or more types to be attached to one another in block form or in random form,
m is an integer from 2 to 200,
$R_{11}$ is hydrogen or methyl;
and
  (iv) optionally, a crosslinking monomer;
wherein the formed ter-polymer is optionally at least partially neutralized with a fatty amine, fatty amine oxide or fatty quaternary.

What is meant by the proviso that if $R_{10}$ is other than hydrogen means that Formula (III) is not for example, dialydimethyammonium chloride (DADMAC).

The invention also encompasses personal cleansing or personal care compositions comprising the conditioning polymer described above.

The personal care compositions of particular interest are those personal care compositions which are applied to the body, including the skin and hair.

These personal care or personal cleansing compositions comprising the conditioning polymer described above may be dispersed or soluble in a cosmetically acceptable medium which medium optionally further comprises a detersive anionic surfactant and/or a silicone.

Personal cleansing or personal care compositions comprising the conditioning polymer described above may further comprise at least one surfactant chosen from anionic, amphoteric, nonionic and zwitterionic surfactants. Preferably, the surfactant is an anionic detersive surfactant.

The personal cleansing or personal care compositions of particular interest are personal cleansing compositions which are shampoos or bodywashes.

Of special interest are "2 in 1" shampoos containing the inventive ter-polymer.

Thus a shampoo or bodywash, preferably a 2 in 1 shampoo comprising the conditioning ter-polymer described above which shampoo or bodywash optionally further contains a detersive anionic surfactant and/or a silicone are claimed.

Several method embodiments are envisioned.

A process for washing and/or conditioning a keratinous substrate comprising treating the keratinous substrate with an effective amount of a composition comprising the polymer described above, optionally further comprising an anionic surfactant and/or a silicone.

A method for enhancing the deposition of silicone, fatty quaternaries, fatty amines, fatty amine oxides and other conditioning actives onto skin, hair or nails which comprises topically applying to said skin, hair or nails a composition comprising
   i.) the polymer described above;
   ii) at least one silicone compound
and
optionally,
an effective amount of a benefit agent to a desired location on the skin, hair, and/or nails.

DETAILED DESCRIPTION OF THE INVENTION

Definitions

Other than in the operating examples, or where otherwise indicated, all numbers expressing quantities of ingredients or reaction conditions used herein are to be understood as modified in all instances by the term "about".

"Molecular weight" means average molecular weight (Mw) expressed as g/mole.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified.

Monomers are ethylenically unsaturated compounds capable of being polymerized.

A monomer unit is the unit that is formed from the ethylenically unsaturated compound after polymerization.

Amphoteric or ampholytic may be used interchangeably, and describe a polymer that comprises anionic monomeric units and cationic monomeric units. An ampholytic polymer may be: anionic at a pH that is higher than its isoelectric point; and cationic at a pH that is lower than its isoelectric point: wherein the isoelectric point is the pH at which the net charge on a polymer is zero.

(Meth)acryl refers to both the acrylic and methacrylic derivatives.

The term "polymer" as used herein shall include materials whether made by polymerization of one type of monomer or made by two (i.e., copolymers) or more types of monomers.

The term "ter-polymer" for purposes of the invention means a polymer formed from at least three different monomers.

The term "water soluble" as used herein, means that the polymer is soluble in water in the present composition. In general, the polymer should be soluble at 25° C. at a concentration of 0.1% by weight of the water solvent, preferably at 1%, more preferably at 5% and most preferably at 15%.

Keratinous substrates are human or animal skin, hair or nails.

The term "skin" as used herein includes the skin on the face, neck, chest, back, arms, hands, legs and scalp.

As used herein, the term "effective amount" refers to that amount of a composition necessary to bring about a desired result, such as, for example, the amount needed to condition a keratin-containing substrate.

The compositions of the present invention preferably comprise a cosmetically acceptable vehicle or carrier. This phrase "cosmetically acceptable vehicle or carrier", as used herein, means one or more compatible solid or liquid fillers, diluents, extenders and the like, which are cosmetically acceptable. As used herein "cosmetically acceptable" means a material (e.g., compound or composition) which is suitable for use in contact with human skin, hair or nails. The type of carrier or vehicle utilized in the present invention depends on the type of product desired. The compositions useful in the present invention may be a wide variety of product types. These include, but are not limited to, shampoos, rinse-off conditioners, lotions, creams, gels, sprays, pastes, mousses, and suspensions.

The Conditioning Ter-Polymer

The novel conditioning polymer of the invention is formed from at least three monomers, i.) a cationic monomers encompassed by formula (1), $$R_1-\underset{H}{\overset{R_2}{C}}=\underset{O}{\overset{R_3}{C}}-X-L-\overset{R_3}{\underset{R_5}{N^+}}-R_4 \quad A^- \quad (I)$$

in which:

$R_1$ and $R_2$ are independently hydrogen or methyl, $R_3$, $R_4$ and $R_5$ are independently linear or branched $C_1$-$C_{30}$ alkyl radicals, X is NH, $NR_6$ or oxygen, preferably X is NH or $NR_6$ and most preferably X is NH, $R_6$ is $C_1$-$C_6$ alkyl, L is $C_nH_{2n}$, n is an integer from 1 to 5, and A– is an anion derived from an organic or inorganic acid, such as a methosulphate anion or halide, such as chloride or bromide, ii.) at least one anionic monomer selected from the group consisting of ethylenically unsaturated carboxylic acid and sulfonic acid containing monomers;
and
   iii.) a diallyl amine defined by formulae (II) or (III)

$$\underset{R_7}{\overset{}{\diagup}}\overset{}{\underset{R_9}{N}}\underset{R_8}{\overset{}{\diagdown}} \quad (II)$$

$$\underset{R_7}{\overset{}{\diagup}}\overset{R_{10}}{\underset{R_9}{N^+}}\underset{R_8}{\overset{}{\diagdown}} \quad (III)$$

in which, $R_7$ and $R_8$ are independently hydrogen or $C_1$-$C_4$ alkyl,
and
$R_9$ is hydrogen, branched or linear $C_1$-$C_{30}$ alkyl,

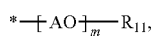

$C_1$-$C_{30}$ alkoxy, hydroxy substituted $C_1$-$C_{10}$ alkyl, $C_7$-$C_9$ alkylphenyl, carboxyalkyl, alkoxyalkyl and carboxyamidalkyl,
$R_{10}$ is hydrogen, $C_1$-$C_{20}$ alkyl, $C_5$-$C_{10}$ cycloalkyl or an unsubstituted or substituted benzyl radical, preferably $R_{10}$ is hydrogen, $C_1$-$C_4$ alkyl or benzyl, most preferably $R_{10}$ is hydrogen; with the proviso that if $R_{10}$ is other than hydrogen, then $R_9$ is

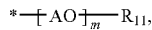

AO is a $C_1$-$C_{12}$ alkylene oxide or mixtures of two or more types thereof, it being possible for the two or more types to be attached to one another in block form or in random form, n is an integer from 2 to 200,
$R_{11}$ is hydrogen or methyl;
and
  iv.) optionally a crosslinking monomer,
wherein the formed ter-polymer is optionally at least partially neutralized or complexed with a fatty amine, fatty amine oxide or fatty quaternary.

In regard to formula (I), $R_3$, $R_4$ and $R_5$ are for example $C_1$-$C_{14}$, $C_1$-$C_8$, $C_1$-$C_6$ or $C_1$-$C_4$. Most typically $R_3$, $R_4$ and $R_5$ are $C_1$-$C_4$ such as methyl, ethyl, propyl, butyl or a mixture thereof.

The cationic monomer of formula (I) used in the inventive conditioning ter-polymer is for example selected from the group consisting of
(meth)acryloyloxyethyl-N,N,N-trimethylammonium chloride,
(meth)acryloyloxyethyl-N-ethyl-N,N-dimethylammonium monoethyl sulfate,
(meth)acryloyloxyethyl-N,N,N-triethylammonium monoethyl sulfate,
(meth)acryloylaminopropyl-N,N,N-trimethylammonium chloride,
(meth)acryloylaminopropyl-N-ethyl-N,N-dimethylammonium monoethyl sulfate,
(meth)acryloylaminopropyl-N,N-diethyl-N-methylammonium chloride,
(meth)acryloylaminopropyl-N,N-diethyl-N-methylammonium monomethyl sulfate and mixtures thereof,
preferably (meth)acryloylaminopropyl-N,N,N-trimethylammonium chloride,
(meth)acryloylaminopropyl-N-ethyl-N,N-dimethylammonium monoethyl sulfate,
(meth)acryloylaminopropyl-N,N-diethyl-N-methylammonium chloride,
(meth)acryloylaminopropyl-N,N-diethyl-N-methylammonium monomethyl sulfate and mixtures thereof and
especially acryloylaminopropyl-N,N,N-trimethylammonium chloride.

X is preferably NH.

The cationic monomer of formula (I) or component i.) will for example make up at least about 10 to about 98 weight percent of the formed conditioning ter-polymer.

Alternatively, for example the cationic monomer of formula (I) makes up about 40 to about 96 or about 40 to about 94 weight percent of the total weight of the formed ter-polymer. A minimum of about 40 or 50 weight % component i.) is most typical.

The anionic monomers of component ii.) will typically contain carboxylic acids or sulfonic acid groups. For example, acrylic acid (AA), methacrylic acid (MAA), 2-acrylamido-2-methylpropane sulfonic acid (AMPSA), 2-methacrylamido-2-methylpropane sulfonic acid (MAMPSA), crotonic acid, 2-methyl crotonic acid, maleic acid, maleic anhydride, itaconic acid, itaconic anhydride and mixtures thereof are considered.

For example, the conditioning ter-polymer is formed from anionic monomers of component ii.) which are monoethylenically unsaturated $C_3$-$C_6$ monocarboxylic acids, such as acrylic acid, methacrylic acid, crotonic acid, isocrotonic acid, 2-ethylpropenoic acid or ethylenically unsaturated $C_4$-$C_6$ dicarboxylic acids, such as maleic acid, fumaric acid, itaconic acid or the anhydrides thereof, for example maleic anhydride, or the sodium, potassium or ammonium salts thereof.

The anionic monomer of component ii.) are especially compounds of formula (VI) or the anhydrides thereof:

where
$R_{12}$ and $R_{13}$ are independently hydrogen or $C_1$-$C_6$ alkyl,
$R_{14}$ is hydrogen, $C_1$-$C_6$ alkyl or a COOM group and
M is hydrogen, a monovalent or divalent metal ion, ammonium or an organic ammonium ion.

A particularly preferred embodiment is the conditioning polymer, wherein the anionic monomer of component ii.) is a compound of formula (VI) or the anhydrides thereof:

$R_{12}$ and $R_{13}$ are independently hydrogen or $C_1$-$C_6$ alkyl,
$R_{14}$ is hydrogen, $C_1$-$C_6$ alkyl or a COOM group,
M is hydrogen, a monovalent or divalent metal ion, ammonium or an organic ammonium ion,
$R_9$ and $R_{10}$ of the diallyl component iii.) are hydrogen
and
the formed ter-polymer is at least partially neutralized with a fatty amine or a fatty amine oxide.

The anionic monomer or component ii.) will preferably make up at least 2 to about 25, about 4 to about 20, about 5 to about 15 weight percent of the total weight of the formed conditioning polymer.

Most often component ii.) will more preferably not exceed 20 or 30 wt. %. For example, the component ii) will most often be a minimum of about 3 or 4 wt. % and a maximum of about 20 wt. %.

The molar ratio of component i.) and ii.) may vary from 12:1 to 3:1, preferably for example 10:1 to 4:1. Thus the ter-polymer will always carry a cationic charge regardless of the pH of the medium in which the ter-polymer is dispersed or dissolved.

Component iii.) monomer is for example diallyamine.

The amine of the diallyamine may be substituted by $R_9$ and/or $R_{10}$.

$R_9$ is defined as hydrogen, branched or linear $C_1$-$C_{30}$ alkyl,

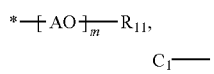

$C_{30}$ alkoxy, hydroxy substituted $C_1$-$C_{10}$ alkyl, $C_7$-$C_9$ phenylalkyl, carboxyalkyl, alkoxyalkyl and carboxyamidalkyl.

* represents the connection to the nitrogen of the diallyamine.

Linear or branched $C_1$-$C_{30}$ alkyl is for example alkyl having $C_1$-$C_4$, $C_1$-$C_6$, $C_1$-$C_8$, $C_1$-$C_{10}$, $C_1$-$C_{12}$, $C_1$-$C_{14}$, $C_1$-$C_{16}$, $C_1$-$C_{18}$, $C_1$-$C_{20}$, $C_1$-$C_{22}$, $C_1$-$C_{24}$, $C_1$-$C_{26}$ or $C_1$-$C_{28}$. Specific examples include methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, stearyl, lauryl, cetyl, octadecyl, icosyl or docosyl.

$C_1$-$C_{12}$ alkylene oxide is for example $CH_3$—O—$CH_2$—, $CH_3$—(O—$CH_2CH_2$—)$_2$O—$CH_2$—, $CH_3$—(O—$CH_2CH_2$—)$_3$O—$CH_2$— or $CH_3$—(O—$CH_2CH_2$—)$_4$O—$CH_2$—.

For example $R_9$ may be substituted by polyethyleneoxide or polypropyleneoxide or a mixture thereof.

Such substituted alkyoxalated diallyamines are disclosed in U.S. Pat. Nos. 7,579,421 and 5,478,883 herein incorporated entirely by reference.

For example, formulae (II) or (III) may be a monomer, wherein $R_9$ is

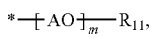

AO is $C_1$-$C_{12}$ alkylene oxide or a mixture of two or more types thereof, it being possible for the two or more types to be attached to one another in block or in random form,
m is an integer from 1 to 200,
and $R_{11}$ is hydrogen or methyl.

The diallyamine may be compounds of formula (II) or (III):

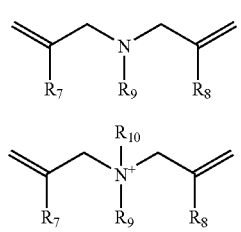

A particularly preferred monomer of (II) or (III) is

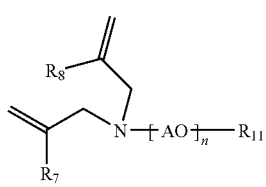

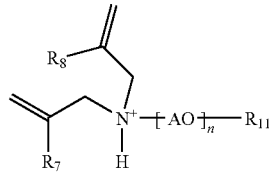

wherein AO is $C_2$-$C_4$ alkylene oxide such as ethylene oxide, propylene oxide, 1-butylene oxide, isomers of butylene oxide and mixtures thereof it being possible for the two or more types of alkylene oxides to be attached to one another in block or in random form, $R_8$ and $R_7$ are as defined above,
and $R_{11}$ is hydrogen or methyl.

A preferred monomer formula of (IIa) or (IIIa) is formed by the reaction of diallyamine with about 10 to 30 wt. percent propylene oxide and about 90 to 70 wt. percent ethylene oxide and the average molecular weight of the diallyamine of formula (IIa) and (IIIa) is about 500 to about 3500.

Another especially preferred compound of formula (II) is diallyamine, wherein $R_9$ is hydrogen
and formula (III) is the protonated salt ($R_9$ and $R_{10}$ are hydrogen).

$C_7$-$C_9$-phenylalkyl is for example, benzyl, α-methylbenzyl, α, α-dimethylbenzyl or 2-phenylethyl.

Carboxyalkyl is for example —$COCH_2CH_3$, —$CO(CH_2)_n$ $CH_3$, wherein n is 1-4, 1-6, 1-8, 1-10, 1-12 or 1-16, or —$COCH_2CH(CH_3)_2$. Thus the alkyl of carboxyalkyl may be branched or linear and will vary in carbon number from $C_2$-$C_{24}$, $C_2$-$C_{20}$, $C_2$-$C_{18}$, $C_2$-$C_{12}$, $C_2$-$C_8$ or $C_2$-$C_6$ carbons.

Carboxyamidalkyl is analogous to carboxyalkyl above. Carboxylamidalkyl is for example, —$CONCH_2CH_3$, —$CON(CH_2)_nCH_3$, wherein n is 1-4, 1-6, 1-8, 1-10, 1-12 or 1-16, or —$COCH_2CH(CH_3)_2$. Thus the alkyl of carboxyalkyl may be branched or linear and will vary in carbon number from $C_2$-$C_{24}$, $C_2$-$C_{20}$, $C_2$-$C_{18}$, $C_2$-$C_{12}$, $C_2$-$C_8$ or $C_2$-$C_6$. carbons.

Alkoxyalkyl is for example, ethoxyethyl, propoxymethyl, methoxymethyl, methoxyethyl, ethoxybutyl, ethoxyoctyl etc. The carbon number of the alkoxy will for examples vary from $C_1$-$C_6$. The alkyl of the alkoxyalkyl will for example vary from $C_1$-$C_{18}$, $C_1$-$C_{12}$, $C_1$-$C_8$ or $C_1$-$C_6$.

Hydroxy substituted $C_1$-$C_{10}$ alkyl is for example —CH2CH2—OH, —CH2CH2CH2OH, —CH2CH(OH)CH2CH2OH. The alkyl of the $C_1$-$C_{10}$ alkyl may for example range from $C_1$-$C_8$, $C_1$-$C_6$, $C_1$-$C_4$. or $C_1$-$C_2$. The alkyl for instance, may be mono, di or tri hydroxyl substituted.

Suitable diallyamines of formula (II) are for example diallyamine, diallymethylamine, diallyethylamine, diallypropylamine, diallybutylamine, diallyhydroxymethylamine, diallyhydroxyethylamine, diallyhydroxypropylamine, diallylethoxyethylamine and diallyhydroxylbutylamine.

Diallyamines do not function as crosslinking agents although the monomers are diolefinic. Instead the monomer polymerizes to form a pyrrolidine ring as part of the polymer backbone as below.

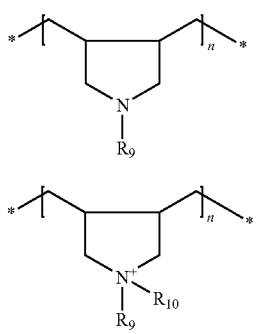

Component iii.) may make up about 2.0 to about 40 weight percent or makes up for example about 2, 3, 4, 5, 6, 7, 8, 9, 10, 12, 15, 18, 20, 30 or 35 weight percent of total weight of the formed polymer.

The component iii.) may make up from about 2 to about 40, about 3 to about 35, or about 3 to about 30 weight percent of the total weight of formed polymer.

The weight percent of component iii.) in the formed ter-polymer will depend very much on the molecular weight of the component iii). For example when $R_9$ of component iii) is

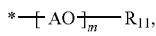

the average molecular weight of the monomer may vary from 500 to 3500.

When the conditioning ter-polymer is formed from monomers such as (IIa) and (IIIa)

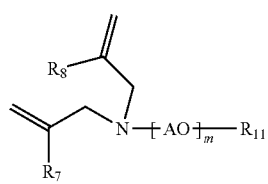

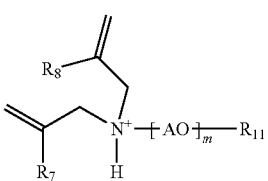

the polymerized monomer units of IIa and/or IIIa make up from about 6 or 7 to about 35, 8 to about 30 wt. percent of the formed conditioning ter-polymer.

Further (IIa) and (IIIa) monomers have surfactant properties. The alkylene oxide substituted monomers show a hydrophilic-lipophilic balance which is determined by the particular $C_1$-$C_{12}$ alkylene oxide and the number of repeating units. The preferred monomers of (IIa) and (IIIa) used to form the conditioning ter-polymer are characterized by an HLB from 5 to about 18.

The diallyamine monomer component iii.) of formula (IIa) and (IIIa) above is characterized by an average molecular weight (via GPC) of about 500 to about 3500, preferably from about 800 to about 3000 and most preferably from about 1000 to about 3000.

A particularly preferred conditioning polymer comprises a monomer of formula (IIa) or (IIIa) formed by the reaction of diallyamine with about 10 to 30 wt. percent propylene oxide and about 90 to 70 wt. percent ethylene oxide.

Further the conditioning ter-polymer formed using the diallyamine monomer component iii.) of formula (IIa) and (IIIa) above is characterized by a hydrophilic-lipophilic balance of between 5 and 18, preferably 6 to 17.

HLB values are calculated using Davis equation that uses the group contributions:

$$HLB = 7 + \Sigma H \text{ (hydrophilic group numbers)} - \Sigma L \text{ (lipophilic group numbers)}$$

where $\Sigma H$ is the sum of contributions of hydrophilic groups, and $\Sigma L$ is the sum of contributions of hydrophobic groups.

The calculation methods are further described within Davis, J. T., Rideal, E. K. *Interfacial Phenomena* 1963, $2^{nd}$ Ed., Academ. Press, London and Davis, J. T. *Proc. Int. Congr. Surf. Act.* $2^{nd}$, 1957, 1, 426-438.

The formed ter-polymer will for example carry a net positive charge. This net positive charge is primarily due to the monomer unit of formula (I) and is independent of the ter-polymer matrix or formulation environment. However, the diallyamine monomer unit may also contribute to the total cationic charge of the formed ter-polymer when in an acidic environment. As shampoo formulations are typically slightly acidic ie. 5 to about 6.5, the diallyamine monomer unit of formula (III) will likely be protonated giving additional cationic charge to the formed ter-polymer ($R_{10}$ will be hydrogen).

The total charge density of the formed ter-polymer will to some extent be dependent on the pH of the medium. However, the charge density will vary from about 0.2 to about 6 or 7 mequiv./gram. For instance, the charge density will vary from about 0.5 to about 6 or about 1 to about 5 mequiv/gram. Typically the charge density of the ter-polymer in a slightly acidic environment will vary from about 1.0 to about 4.5 or about 2 to about 3.8.

The negative charge (from the anionic monomer or component ii)) in the formed polymer may optionally be neutralized or form a complex or coacervate with a fatty amine, a fatty amine oxide, or a fatty quaternary either by adding the fatty amines, oxides or fatty quaternary during the polymerization process or after the polymerization process. For example, the negative charge produced by the acidic monomer may be neutralized prior to polymerization then polymerized. Alternatively, the fatty amine, or fatty amine oxide, or fatty quaternary may simply be added after formation of the amphoteric polymer. Preferably, the fatty amine, or fatty amine oxide, or fatty quaternary is added after the amphoteric polymer is formed if added at all.

Personal cleansing or personal care composition comprising the conditioning ter-polymer along with a conditioning agent in one embodiment of the invention may exist in a complex coacervate form upon dilution of water or upon addition of the inventive ter-polymer to the formulation. The coacervate may include complexation with the conditioning agents such as a fatty amine, fatty amine oxide, fatty quaternary defined below, silicone, oil, or emollient also defined below.

Fatty Amines, and Fatty Amine Oxides, and Fatty Quaternaries

These fatty amines are essentially cationic surfactants.

Fatty Amines

Fatty amines useful to compositions of the present invention include primary, secondary and tertiary amines.

Fatty amines or salts thereof having the formula

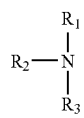
(IV)

wherein $R_1$ is a $C_8$-$C_{30}$ straight or branched chain aliphatic, $R_2$ and $R_3$ are independently hydrogen, $C_1$-$C_{30}$ straight or branched chain aliphatic, hydroxyalkyl, amidoalkyl, carboxyalkyl, cyclic, alkoxy, polyalkoxy, or hydroxypolyalkoxy group function as useful fatty amines. For example, $R_2$ and $R_3$ are independently $C_1$-$C_8$ alkyl or $C_1$-$C_6$ alkyl.

Nonlimiting examples of the primary, secondary and tertiary fatty amines thereof are octylamine, decylamine, dodecylamine, tetradecylamine, hexadecylamine, octadecylamine, laurylamine, myristylamine, stearylamine, eicosylamine, docosylamine, coco amine, oleylamine, tallow amine, hydrogenated-tallow amine, soya amine, dioctylamine, didecylamine, didodecylamine, ditetradecylamine, dihexadecylamine, dicocoamine, dehydrogenated-tallow amine, dioctadecylamine, N-methyldioctadecylamine, N,N-dimethyldodecylamine, N,N-dimethylmyristylamine, N,N-dimethylstearylamine and N,N-dimethyloctadecylamine.

Myristylamine although defined as tetradecamine is more likely a blend of $C_{12}$, $C_{14}$ and $C_{16}$ homologues.

Stearylamine is analogous in that stearyl is octadecamine but is more likely a blend of $C_{16}$, $C_{18}$ and $C_{20}$.

Laurylamine is defined as dodecylamine however is more likely a blend of $C_{10}$, $C_{12}$ and $C_{14}$ homologues.

Mixtures of the above fatty amines may also be used.

Fatty Amine Oxides

Long chain tertiary amine oxides corresponding to the following general formula:

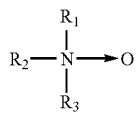
(V)

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond.

Non-limiting examples of amine oxides suitable for use in this invention include dimethyl-dodecylamine oxide, oleyidi (2-hydroxyethyl) amine oxide, dimethyloctylamine oxide, dimethyl-decylamine oxide, dimethyl-tetradecylamine oxide, 3,6,9-tri-oxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide, myristyldimethyl amine oxide and stearyldimethyl amine oxide.

Fatty Quaternaries

Suitable cationic surfactants for charge neutralization of the ter-polymer are mono- and dialkyl quats corresponding to the following formula.

Formula (VI)

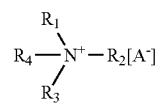
(VI)

Mono long chain alkyl quats suitable for use herein include Formula (VI) conditioning surfactants wherein $R_1$, $R_2$, and $R_3$, which may be the same or different, are $C_1$-$C_4$ alkyl groups (ie. ethyl or methyl) and $R_4$ is a $C_8$ or greater aliphatic hydrocarbyl group (preferably $C_{14}$ to $C_{22}$ alkyl). Other alkyl quats suitable for use herein are Formula (VI) conditioning surfactants wherein $R_1$ and $R_2$, which may be the same or different, are $C_1$-$C_4$ alkyl groups (ie. ethyl or methyl), $R_3$ is an aryl group, for example benzyl, and $R_4$ is a $C_8$ or greater aliphatic hydrocarbyl group (for example $C_{14}$ to $C_{22}$ alkyl). [A] can be chloride, bromide, or methosulfate. The monoalkyl quats may, but need not, be in the form of mixtures. Non-limiting examples of mono alkyl quats are:

cetyltrimethylammonium chloride (C16);
stearyltrimethylammonium chloride (C18);
behenyltrimethylammonium chloride (C22);
cetyltrimethylammonium bromide (C16);
tallowtrimonium chloride (C16/C18);
behenyltrimethylammonium methosulfate (C22);
palmityltrimethylammonium chloride (C16);
hydrogenated tallowtrimethylammonium chloride (C16/C18);
hydrogenated tallowtrimethylammonium bromide (C16/C18);
hydrogenated tallowtrimethylammonium methosulfate (C16/C18);
cetrimonium tosylate (C16): and
eicosyltrimethylammonium chloride (C20).

Also included in Formula (VI) are dialkyl quats in which $R_1$ and $R_2$, which may be the same or different, are $C_1$-$C_4$ alkyl groups and $R_3$ and $R_4$, which may be the same or different, are $C_8$ or greater aliphatic hydrocarbyl groups (for example $C_{14}$ to $C_{22}$ alkyl). If desired, the dialkyl quats may be in the form of mixtures. Non-limiting examples of dialkyl quats are:

dimethyldicetylammonium chloride (C16);
dimethyldistearylammonium chloride (C18);
dimethyldipalmitylammonium chloride (C16);
dimethyl(dihydrogenatedtallow)ammonium chloride (C16/C18);
dimethyl(ditallow)ammonium chloride (C16/C18)
dimethyl(dihydrogenatedtallow)ammonium bromide (C16/C18)
dimethyl(dihydrogenatedtallow)ammonium methosulfate (C16/C18)

Desirably, the level of cationic surfactant to neutralize the ter-polymer varies from about 0.1 to about 5 percent by weight, based on the total weight of the ter-polymer. In the practice of this invention, the cationic surfactants can also be mixtures of monoalkyl quats and dialkyl quats wherein the ratio of the monoalkyl quat to dialkyl quat is from 15:1 to 1:0.5, more particularly from 0:1 to 1:1 are of particular interest.

The weight ratio of fatty quaternary, fatty amine or fatty amine oxide to ter-polymer may vary for example, from about 1:5 to about 5:1, alternatively about 1:3 to about 3:1 or more typically about 1:2 to about 1:2.

The novel amphoteric ter-polymer may comprise additional monomers other than those defined by the monomer groups i.), ii.) and iii.).

For example the amphoteric polymer may optionally also contain additional nonionic monomers, For example the amphoteric polymer may optionally also contain at least one monomer selected from the group consisting of $C_1$-$C_{22}$ straight or branched chain alkyl acrylates or methacrylates, a $C_1$-$C_{22}$ straight or branched chain n-alkyl acrylamide or methacrylamide, $C_1$-$C_6$ hydroxy substituted alkyl acrylates or methacrylates, n-vinylpyrrolidone, vinyl acetate, ethoxylated and propoxylated acrylate or methacrylate and unsubstituted acrylamide.

Suitable nonionic monomers which may optionally be polymerized with the monomers of components i.), ii.) and iii.) are for example acrylamide, hydroxyethyl (meth)acrylate, N,N-dimethyl (meth)acrylamide, N,N-diethyl(meth)acrylamide, N-methyl (meth)acrylamide, N-ethyl (meth)acrylamide, methyl (meth)acrylate, ethyl (meth)acrylate, propyl (meth)acrylate, butyl (meth)acrylate and octyl (meth)acrylate.

The amphoteric polymer may also optionally contain amine containing monomers such as dimethylaminoethyl (meth)acrylate, diethylaminoethyl (meth)acrylate, dimethylaminopropyl (meth)acrylamide, diethylaminoethyl (meth)acrylamide, 2-tert.-butylaminoethyl (meth)acrylate or dimethylaminoneopentyl (meth)acrylate.

Preferably, the amphoteric ter-polymer is formed substantially from monomer units i.), ii.) and ii.) above and optionally crosslinking agents and/or neutralized with fatty amine, fatty amine oxide or fatty quaternaries.

The weight ratio of the conditioning polymer and fatty amine, fatty amine oxide or fatty quaternary ranges from 1:5 to 5:1, preferably 1:3 to 3:1 and most preferably 1:2 to 1:5.

Substantially formed from monomer units i.), ii.) and ii.) above and optionally crosslinink agents and/or neutralized with fatty amine, fatty amine oxide or fatty quaternaries means that additional monomers other than those defined in i.), ii.) and iii.) and optional agents may be used to form the ter-polymer but will typically be no more than about 2, 3, 4 or 5 weight percent of the formed ter-polymer.

The amphoteric ter-polymer may consist of monomer components i.), ii.) and iii.), wherein the formed ter-polymer is optionally at least partially neutralized or complexed with a fatty amine, fatty amine oxide or fatty quaternaries and further optionally contains a crosslinking agent.

The average molecular weight (Mw) of the ampholytic conditioning ter-polymer or mixtures thereof ranges for example from about 10,000 to about 18,000,000, about 25,000 to about 5,000,000, typically about 35,000 to about 1,800,000. Alternatively, the Mw may vary from about 15,000 to about 1,000,000 or about 10,000 or about 20,000 to about 800,000. For example, more preferably about 100,000 to about 1,000,000 are envisioned.

The amphoteric polymer may be either water soluble, water-swellable or water dispersible.

The conditioning amphoteric polymer may optionally be cross-linked.

"Cross-linked" as used herein refers to at least two chains of the amphoteric polymer attached by bridges, referred to herein as "cross-linking agents" comprising an element, a group, or a compound which joins certain carbon atoms of the chains by primary chemical bonds. Alternatively, the amine of the pyrrollidine (formed from the diallyl amine) incorporated into the chain of the formed conditioning polymer may also be the site where the chains are joined. For example, U.S. Pat. No. 6,323,306, herein incorporated entirely by reference, teaches the cross-linking of cationic co-polymers with diallyl amine using polyfunctional cross-linking agents.

"Polyfunctional" cross-linking agents may comprise monomers having: at least two double bonds; at least a double bond and a reactive group; or at least two reactive groups.

Suitable cross-linking agents include, but are not limited to, polyfunctional epoxy compounds, dihaloalkyl compounds, diisocyanate compounds and compounds containing at least two activated olefinic double bonds.

Exemplary cross-linking agents of the at least diolefinic variety are methylenebisacrylamide; methylenebismethacrylamide; 1,3-diallylurea, triallylurea, tetraallylurea, N,N-diallylacrylamide, tetraallylammonium chloride, tetraallylammonium sulfate, tetraallylammonium methylsulfate, esters of unsaturated monocarboxylic and polycarboxylic acids with polyols, diacrylates and triacrylates, dimethacrylates and trimethacrylates, butanediol and ethylene glycol diacrylate and methacrylate, diethylene glycol diacrylate, poly(ethylene glycol) diacrylate, poly(propylene glycol) diacrylate and the like, trimethylolpropane triacrylate (TMPTA) and trimethylolpropane trimethacrylate (TMPTMA). Allyl compounds may also be considered such as allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives. MBA is the most typical cross-linking agent.

Examples of polyfunctional epoxy compounds include epihalohydrins such as epichlorohydrin, ethylene glycol diglycidyl either (EGDE); diglycidyl ether; 1,2,3,4-diepoxybutane; 1,2,5,6-diepoxyhexane; poly(propylene glycol) diglycidyl ether (PPGDE); 1,4-butanediol diglycidyl ether, 3-bis (glycidyloxy)methyl-1,2-propanediol, bisphenol A diglycidyl ether (BADGE), poly(phenylglycidyl ether-co-formaldehyde), glycerol propoxylate triglycidyl ether, N,N-diglycidyl-4-glycidyloxyaniline, triglycidyl isocyanurate and the like.

Examples of dihaloalkyl compounds include 1,2-dichloroethane, 1,2-dibromoethane, 1,3-dichloropropane, 1,4-dichlobutane, 1,6-dichlorohexane, 1,10-dichlorodecane and the like. Preferred dihaloalkyl cross-linkers are 1,2-dibromoethane and 1,2-dichloroethane.

Diisocyanate compounds can be used as the cross-linking agent for base polymers containing primary or secondary amino groups. Examples of diisocyanate compounds are isophorone diisocyanate (IPDI), 1,4-diisocyanobutane, hexamethylene diisocyanate (HDI), toluene diisocyanate (TDI) and the like.

The polyfunctional cross-linking units may be added during the formation of the amphoteric polymer at amounts that range from 20 to 10,000 ppm of the total monomer content. For example, 20 to 1000 ppm, 50 to 800 ppm or 75 to 600 ppm are envisioned.

Typical crosslinkers are methylenebisacrylamide (MBA); methylenebismethacrylamide.

The weight fraction of crosslinking comonomers, based on the total mass of the copolymers, is not more than 5%, 3% or 2% by weight, more typically from 0.00002 to 2% by weight, and most preferably from 0.00002 to 1% by weight Use of the Conditioning Ter-Polymer The novel amphoteric ter-polymer may be used in virtually any personal care composition. The amphoteric polymer has been found to be especially useful in personal care compositions which are used on keratinous substrates such as hair, skin or nails. Such products as shampoos, conditioners, rinses, coloring products, bleaching products, setting lotions, blow-drying lotions, restructuring lotions, perms and straightening products may incorporate the inventive amphoteric polymer.

These personal care compositions comprising the amphoteric polymer may be personal cleansing compositions such as shampoos and bodywashes.

For example the cleansing composition comprising the conditioning ter-polymer is a 2-in-1 shampoo, a bodywash, a facial wash, a bubble bath, soapless cleansers, liquid and bar soap; a shower gel, xfoliating shower gel; a milk bath; moist towelletes; bath effervescent tablets (e.g., bubble bath); a bath/shower gel or a shower cream and may further comprises a detersive anionic surfactant from about 5% to about 50%, preferably from about 8% to about 30%, most preferably from about 10% to about 25% and especially about 12% to about 18%, by weight of the composition.

Of particular interest are conditioning shampoos or 2-in-1 shampoos. These shampoos not only wash but also condition hair. Thus 2-in-1 shampoos are advantageous in that they do not require a second conditioning step after washing the hair.

Thus a preferred embodiment is a personal cleansing composition comprising the conditioning ter-polymer, wherein the cleansing composition is a 2-in-1 shampoo and further comprises a detersive anionic surfactant from about 5% to about 50%.

"Bodywash" encompasses all cleansing vehicles applied to the body. Exemplary forms of cleansing vehicles include, but are not limited to, liquid, bar, gel, foam, aerosol or pump spray, cream, lotion, stick, powder, or incorporated into a patch or a towelette. In addition, soapless cleansers may be used as well. The bodywash can be made into any suitable product form. Thus, as used herein, "bodywash" includes, but is not limited to, a soap including liquid and bar soap; a shower gel; including an exfoliating shower gel; a foaming bath product (e.g. gel, soap or lotion); a milk bath; including a gel cleanser, a liquid cleanser and a cleansing bar; moist towelletes; bath effervescent tablets (e.g., bubble bath); a bath/shower gel; a shower cream.

These personal care compositions incorporating the amphoteric polymer may also be keratinous conditioning compositions such as hand lotions, body lotion, a body spray, mist or gel, hair conditions rinses, shaving cream, an after-shave, after-shave moisturizer, a depilatory cream; a shaving product e.g. a shaving cream, gel, foam or soap, an after-shave, after-shave moisturizer; a hand and nail cream and combinations thereof, and any other composition used for post-cleansing application to the body, including the skin and hair.

Thus the personal care composition is a hand lotion, body lotion, a body spray, mist or gel, hair conditioning rinse, shaving cream, gel, foam or soap, an after-shave, after-shave moisturizer, a hand and nail cream or a depilatory cream.

As implied above the personal care products can be in any form such as creams, ointments, pastes, foams, gels, lotions, powders, make-ups, sprays, sticks or aerosols.

Creams are oil-in-water emulsions containing more than 50% of water. The oil-containing base used therein is usually mainly fatty alcohols, for example lauryl, cetyl or stearyl alcohol, fatty acids, for example palmitic or stearic acid, liquid to solid waxes, for example isopropyl-myristate or beeswax and/or hydrocarbon compounds, such as paraffin oil. Suitable emulsifiers are surfactants having primarily hydrophilic properties, such as the corresponding non-ionic emulsifiers, for example fatty acid esters of polyalcohols of ethylene oxide adducts, such as polyglycerol fatty acid ester or polyoxyethylenesorbitan fatty acid ether (Tween trademarks); polyoxyethylene fatty alcohol ether or their esters or the corresponding ionic emulsifiers, such as the alkali metal salts of fatty alcohol sulfonates, sodium cetyl sulfate or sodium stearyl sulfate, which are usually used together with fatty alcohols, such as cetyl alcohol or stearyl alcohol. In addition, creams contain agents which reduce water loss during evaporation, for example polyalcohols, such as glycerol, sorbitol, propylene glycol, and/or polyethylene glycols.

Ointments are water-in-oil emulsions which contain up to 70%, preferably not more than 20 to 50%, of water or of an aqueous phase. The oil-containing phase contains predominantly hydrocarbons, such as paraffin oil and/or solid paraffin which preferably contains hydroxy compounds, for example fatty alcohol or their esters, such as cetyl alcohol or wool wax for improving the water absorption. Emulsifiers are corresponding lipophilic substances, such as sorbitan fatty acid ester. In addition, the ointments contain moisturisers such as polyalcohols, for example glycerol, propylene glycol, sorbitol and/or polyethylene glycol as well as preservatives.

Rich creams are anhydrous formulations and are produced on the basis of hydrocarbon compounds, such as paraffin, natural or partially synthetic fats, for example coconut fatty acid triglycerides or preferably hardened oils and glycerol partial fatty acid esters.

Pastes are creams and ointments containing powdered ingredients which absorb secretions, for example metal oxides, such as titanium dioxide or zinc oxide, and also tallow and/or aluminium silicates which bind the moisture or the absorbed secretion.

Foams are liquid oil-in-water emulsions in aerosol form. Hydrocarbon compounds are used, inter alia, for the oil-containing phase, for example paraffin oil, fatty alcohols, such as cetyl alcohol, fatty acid esters, such as isopropylmyristate and/or waxes. Suitable emulsifiers are, inter alia, mixtures of emulsifiers having predominantly hydrophilic properties, for example polyoxyethylenesorbitan fatty acid ester, and also emulsifiers having predominantly lipophilic properties, for example sorbitan fatty acid ester. Commercially available additives are usually additionally employed, for example preservatives.

Gels are, in particular, aqueous solutions or suspensions of active substances in which gel formers are dispersed or swelled, in particular cellulose ethers, such as methyl cellulose, hydroxyethyl cellulose, carboxymethyl cellulose or vegetable hydrocolloid, for example sodium alginate, tragacanth or gum arabic. The gels preferably additionally contain also polyalcohols, such as propylene glycol or glycerol as moisturizers and wetting agents, such as polyoxyethylenesobitan fatty acid ester. The gels furthermore contain commercially available preservatives, such as benzyl alcohol, phenethyl alcohol, phenoxyethanol and the like.

As discussed above, the inventors have discovered that the amphoteric polymer performs very well as a silicone deposition agent. That is when combined in shampoo or bodywash containing silicone, the amphoteric polymers effectively aids in the deposition of silicone onto keratinous surfaces such as hair and skin thus heightening conditioning effects.

The inventive ter-polymer upon dilution as mentioned above may form a ter-polymer/silicone aggregate or coacervate/optional benefit agent (such as fatty amines, fatty amine oxides or quaternary amines, oily components, fatty acids, silicone or mixtures thereof), thus physically depositing the aggregate onto the skin or hair where the conditioning benefit is desired.

The present amphoteric polymer may be used in a personal cleansing composition or a personal care composition at about 0.05 to about 5, about 0.1 to about 3, about 0.1 to about 0.75, about 0.1 to about 0.5 weight percent of the total personal care or personal cleansing composition.

Conditioning Agents

In addition to the fatty amines, fatty amine oxides and quaternary amines, other conditioning agents may be combined with the inventive ter-polymer. For example, conditioning agents useful herein include silicones, oily or fatty materials such as hydrocarbons, fatty ester, silicones and cationic fatty materials such as the fatty amines, fatty oxides, fatty quaternaries suggested above.

Silicones

The most commonly used conditioning agents are silicones. The present amphoteric polymer is effective as a silicone deposition aid with virtually any silicone. The most commonly used silicones which are suitable for use in personal cleansing or personal care compositions are typically modified or unmodified polyorganosiloxanes, i.e. polyorganosiloxane oils or polyorganosiloxane gums or resins, in their native form or in the form of solutions in organic solvents or alternatively in the form of emulsions or microemulsions.

Among the polyorganosiloxanes which may be used in accordance with the present invention, mention may be made, in a non-limiting manner, of:

I. Volatile silicones: these have a boiling point of between 60 C and 260 C. They are chosen from cyclic silicones containing from 3 to 7 and preferably 4 to 5 silicon atoms. Examples of these are octamethylcyclotetrasiloxane sold under the name VOLATILE SILICONE 7207" by Union Carbide or SILBIONE 70045 V2 by Rhone-Poulenc, decamethylcyclopentasiloxane sold under the name VOLATILE SILICONE 715811 by Union Carbide, SILBIONE 70045 V5 by Rhone-Poulenc, as well as mixtures thereof. Mention is also made of cyclocopolymers such as dimethylsiloxane/methylalkylsiloxane, for instance VOLATILE SILICONE FZ3109 sold by the company Union Carbide, which is a dimethylsiloxane/methyloctylsiloxane cyclocopolymer.

II. Non-volatile silicones: these consist mainly of:

(i) polyalkylsiloxanes; among the polyalkylsiloxanes which may mainly be mentioned are linear polydimethylsiloxanes containing trimethylsilyl end groups, such as, for example, and in a non-limiting manner, the SILBIONE oils of the 70047 series sold by Rhodia Chimie; the DC200 oils and Silicone emulsions such as DC-1664 from Dow Corning, and PDMSs containing hydroxydimethylsilyl end groups;

(ii) polyarylsiloxanes;

(iii) polyalkylarylsiloxanes; mention may be made of linear and branched polymethylphenylsiloxanes, polydimethylmethylphenylsiloxanes and polydimethyldiphenylsiloxanes, such as, for example, the oil RHODORSIL 76311 from Rhodia Chimie;

(iv) silicone gums; these are polydiorganosiloxanes with a molecular mass of between 200,000 and 5,000,000, which are used alone or as a mixture in a solvent chosen from volatile silicones, polydimethylsiloxane (PDMS) oils, polyphenylmethylsiloxane (PPMS) oils, isoparaffins, methylene chloride, pentane, dodecane, tridecane, tetradecane or mixtures thereof; mention is made, for example, of the following compounds:

polydimethylsiloxane,
poly[(dimethylsiloxane)/(methylvinylsiloxane)],
poly[(dimethylsiloxane)/(diphenylsiloxane)],
poly[(dimethylsiloxane)/(phenylmethylsiloxane)],
poly[(dimethylsiloxane)/(diphenylsiloxane)/(methylvinylsiloxane)];

mention may also be made, for example, in a non-limiting manner, of the following mixtures:

1) mixtures formed from a polydimethylsiloxane hydroxylated at the end of a chain (Dimethiconol according to the CTFA nomenclature) and from a cyclic polydimethylsiloxane (Cyclomethicone according to the CTFA nomenclature), such as the product Q2 1401 sold by the company Dow Corning;

2) mixtures formed from a polydimethylsiloxane gum with a cyclic silicone, such as the product SF 1214 Silicone Fluid from General Electric, which is an SE 30 gum of molecular weight=500,000 is dissolved in SF 1202 Silicone Fluid (decamethylcyclopentasiloxane);

3) mixtures of two PDMSs of different viscosity, in particular of a PDMS gum and of a PDMS oil, such as the products SF 1236 and CF 1241 from General Electric;

(v) silicone resins; preferably crosslinked siloxane systems containing R2SiO2/2, RSiO3/2 and Si4/2 units in which R represents a hydrocarbon group containing 1 to 6 carbon atoms or a phenyl group. Among these resins, mention may be made of the product sold under the name Dow Corning 593;

(vi) organomodified polyorganosiloxanes; i.e. silicones as defined above, comprising in their general structure one or more organofunctional groups directly linked to the siloxane chain or linked via a hydrocarbonbased radical; mention is made, for example, of silicones comprising:

a) polyethylenoxy and/or polypropylenoxy groups optionally comprising alkyl groups, such as the product known as dimethicone copolyol, sold by the company Dow Corning under the name DC 1248, and alkyl (C12) methicone copolyol sold by the company Dow Corning under the name Q2 5200;

b) (per)fluoro groups such as trifluoroalkyl groups, such as, for example, those sold by the company General Electric under the names FF.150 FLUOROSILICONE FLUID;

c) hydroxyacylamino groups, such as those described in European patent application EP-A-0 342 834, and in particular the silicone sold by the company Dow Corning under the name Q2-8413;

d) thiol groups, such as the silicones X 2-836 from Dow Corning or GP 72A and GP 71 from Genesee;

e) substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, in particular, C1-C4 aminoalkyl or amino (C1-C4) alkylamino (C1-C4) alkyl groups. The silicones known as amodimethicone and trimethylsilylamodimethicone according to the CTFA name (1997) are used more particularly;

f) carboxylate groups, such as the products described in European patent EP 186 507 from Chisso Corporation;

g) hydroxyl groups, such as the polyorganosiloxanes containing a hydroxyalkyl function, described in patent application FR-A-2 589 476;

h) alkoxy groups containing at least 12 carbon atoms, such as the product SILICONE COPOLYMER F 755 from SWS Silicones;

i) acyloxyalkyl groups containing at least 12 carbon atoms, such as, for example, the polyorganosiloxanes described in patent application FR-A-2 641 185;

j) quaternary ammonium groups, such as in the product ABIL K 32701 from the company Goldschmidt;

k) amphoteric or betaine groups, such as in the product sold by the company Goldschmidt under the name ABIL B 9950;

l) bisulfite groups, such as in the products sold by the company Goldschmidt under the names ABIL S 201 and ABIL S 255;

(vii) block copolymers containing a linear polysiloxane-polyalkylene block as repeating unit; the preparation of such block copolymers used in the context of the present invention is described in European patent application EP 0 492 657 A1, the teaching of which is included by way of reference in the present description;

(viii) grafted silicone polymers, containing a non-silicone organic skeleton, consisting of a main organic chain formed from organic monomers containing no silicone, onto which is grafted, within the said chain as well as, optionally, on at least one of its ends, at least one polysiloxane macromonomer; in particular those chosen more preferably from those described in U.S. Pat. Nos. 4,963,935, 4,728,571 and 4,972,037 and patent applications EP-A-0 412 704, EP-A-0 412 707, EP-A-0 640 105 and WO 95/00578, the teachings of which are included in their entirety in the present description by way of non-limiting references;

(ix) grafted silicone polymers, containing a polysiloxane skeleton grafted with non-silicone organic monomers, comprising a main polysiloxane chain onto which is grafted, within the said chain as well as, optionally, on at least one of its ends, at least one organic macromonomer containing no silicone; examples of such polymers, and the particular method for preparing them, are described in particular in patent applications EP-A-0 582 152, WO 93/23009 and WO 95/03776, the teachings of which are included in their entirety in the present description by way of non-limiting references;

(x) or mixtures thereof.

The polyorganosiloxanes preferably used according to the invention are non-volatile polyorganopolysiloxanes and preferably polydimethylsiloxane oils or gums that are optionally aminated, arylated or alkylarylated.

Copending U.S. Ser. No. 12/286,260 herein incorporated entirely by reference describes a modified silicone. The present ampholytic ter-polymer may be used in combination with the therein taught silicone derivatives as an effective deposition aid in personal care compositions.

The polyorganosiloxanes are used in the compositions of the invention in proportions of between 0.01% and 20% by weight and preferably between 0.1 and 10% by weight, relative to the total weight of the composition.

Non-Silicone Conditioning Agents

Compositions according to the present invention may comprise a dispersed, non-volatile, water-insoluble oily non-silicone conditioning agent.

Suitable oily or fatty materials are selected from hydrocarbon oils, fatty esters and mixtures thereof.

Straight chain hydrocarbon oils may for example contain from about 12 to about 30 carbon atoms. Also suitable are branched chain hydrocarbon oils will preferably contain from about 12 to about 42 carbon atoms. Also suitable are polymeric hydrocarbons of alkenyl monomers, such as $C_2$-$C_6$ alkenyl monomers.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Another suitable material is polyisobutylene.

Suitable fatty esters are characterised by having at least 10 carbon atoms, and include esters with hydrocarbyl chains derived from fatty acids or alcohols, Monocarboxylic acid esters include esters of alcohols and/or acids of the formula $R^1COOR$ in which $R^*$ and $R$ independently denote alkyl or alkenyl radicals and the sum of carbon atoms in $R^f$ and $R$ is at least 10, preferably at least 20. Di- and trialkyl and alkenyl esters of carboxylic acids can also be used.

The viscosity of the conditioning oil itself (not the emulsion or the final hair conditioning composition) is from 350 to 10,000,000 mrr^sec$^{-1}$ at 25° C.

The oily or fatty material is suitably present at a level of from 0.05 to 20, preferably from 0.2 to 10, more preferably from about 0.5 to 5 percent by weight of the composition.

Humectants and Moisturizers

The compositions of the present invention can contain one or more humectant or moisturizing materials. A variety of these materials can be employed and each can be present at a level of from about 0.1% to about 20%, more preferably from about 1% to about 10% and most preferably from about 2% to about 5%. These materials include urea; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. Preferred humectants and moisturizers are glycerol, butylene glycol, hexylene glycol, and mixtures thereof.

Detersive Surfactants

These ampholyte polymers of the invention are particularly compatible with detersive anionic surfactant-containing products such as those used in shampoos or personal cleansing products, generally providing clear formulations without the loss of conditioning properties described above but are also compatible with cationic, nonionic, zwitterionic or amphoteric surfactants.

Suitable anionic detersive surfactant components for use in the shampoo composition herein include those which are known for use in hair care or other personal care cleansing compositions. The concentration of the anionic detersive surfactant component in the shampoo composition should be sufficient to provide the desired cleaning and lather performance, and generally for example in the range from about 5% to about 50%, from about 8% to about 30%, from about 10% to about 25% and from about 12% to about 18%, by weight of the composition.

Preferred anionic surfactants suitable for use in the shampoo compositions are the alkyl and alkyl ether sulfates. These materials have the respective formulae $ROSO_3M$ and $RO(C_2H_4O)_xO_3$-M, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium.

R typically has from about 8 to about 18 carbon atoms, from about 10 to about 16 carbon atoms, from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, about 2 to about 5, about 3, molar proportions of ethylene oxide, and the resulting mixture of molecular species having, for example, an average of 3 moles of ethylene oxide per mole of alcohol, is sulfated and neutralized.

Other suitable anionic detersive surfactants are the water-soluble salts of organic, sulfuric acid reaction products conforming to the formula [$R_1$—$SO_3$-M] where $R_1$ is a straight or branched chain, saturated, aliphatic hydrocarbon radical having from about 8 to about 24, about 10 to about 18, carbon atoms; and M is a cation described hereinbefore.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil.

Typical specific anionic detersive surfactants for use in the personal cleansing compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Suitable amphoteric or zwitterionic detersive surfactants may be used in the personal cleansing compositions and herein include those which are known for use in hair care or skin care cleansing composition, and which contain a group that is anionic at the pH of the cosmetic (such as a shampoo) composition. Concentration of such amphoteric detersive surfactants range for example from about 0.5% to about 20%, from about 1% to about 10%, by weight of the composition.

Amphoteric detersive surfactants suitable for use in the personal cleaning compositions are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate.

Zwitterionic detersive surfactants suitable for use in personal cleaning composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are also envisioned.

The personal cleaning compositions of the present invention may further comprise additional surfactants for use in combination with the anionic detersive surfactant component described hereinbefore. Suitable optional surfactants include nonionic surfactants, cationic surfactants, and combinations thereof. Any such surfactant known in the art for use in hair or personal care products may be used, provided that the optional additional surfactant is also chemically and physically compatible with the essential components of the personal cleaning composition, or does not otherwise unduly impair product performance, aesthetics or stability. The concentration of the optional additional surfactants in the personal cleaning composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the personal cleansing or shampoo compositions are described in McCutcheon's, Emulsifiers and Detergents, 1989 Annual, published by M. C. Publishing Co. which descriptions are incorporated herein by reference.

An especially preferred embodiment of the invention is a personal cleansing or personal care composition comprising the conditioning polymer, wherein the conditioning polymer is dispersed or solublilized in a cosmetically acceptable vehicle and optionally further comprises at least one surfactant chosen from anionic, amphoteric, nonionic and zwitterionic surfactants.

An even more preferred embodiment is a personal cleansing or personal care composition, wherein the personal cleansing composition comprising the conditioning polymer is a shampoo or a bodywash and the personal care composition is any personal care composition which is applied to the body, including the skin and hair.

The personal cleansing composition of special interest is a cleansing composition which for example may be s a 2-in-1 shampoo, a bodywash, a facial wash, a bubble bath, soapless cleansers, liquid and bar soap; a shower gel, xfoliating shower gel; a milk bath; moist towellettes; bath effervescent tablets (e.g., bubble bath); a bath/shower gel or a shower cream, preferably the cleansing composition is a 2-in-1 shampoo and the personal cleansing composition optionally further comprises a detersive anionic surfactant from 5% to 50%, preferably from 8% to 30%, most preferably from 10% to 25% and especially 12% to 18%, by weight of the composition.

Benefit Agents

Benefit agents may be combined with the inventive terpolymer and optionally include conditioning agents such as hydrocarbon oils, fatty esters, silicones, fatty amines, fatty amine oxides and fatty quaternaries. Further benefit agents possible may also include such ingredients as sunscreens, anti dandruff agents, proteins, minerals, herbal extracts, pediculocides, vitamins and UV absorbers.

Optional Ingredients

Further, it is common for personal care preparations to contain suspending agents, viscosity modifiers, dyes, non-volatile solvents or diluents (water soluble and insoluble), pearlescent aids, foam boosters, additional surfactants or nonionic cosurfactants, pH adjusting agents, perfumes, preservatives, chelants, skin active agents, minerals, herbal/fruit/food extracts, sphingolipids derivatives or synthetical derivative, and clay.

Anti-dandruff agents are of particular interest as cationic polymers are well known as aids for depostion of anti-drandruff agents such as pyridinethione salts. For example, U.S. Publication Application Nos. 2008/0206355 teaches cationic homopolymers in combination pyrithione. Thus the compositions of the present invention may also contain an anti-dandruff agent.

Suitable, non-limiting examples of anti-dandruff particulates include: pyridinethione salts, azoles, selenium sulfide, particulate sulfur, and mixtures thereof. Preferred are pyridinethione salts. Such anti-dandruff particulate should be physically and chemically compatible with the essential components of the composition, and should not otherwise unduly impair product stability, aesthetics or performance.

Pyridinethione anti-dandruff particulates, especially 1-hydroxy-2-pyridinethione salts, are highly preferred particulate anti-dandruff agents for use in compositions of the present invention. The concentration of pyridinethione anti-dandruff particulate typically ranges from about 0.1% to about 4%, by weight of the composition, preferably from about 0.1% to about 3%, more preferably from about 0.3% to about 2%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"), more preferably 1-hydroxy-2-pyridinethione salts in platelet particle form, wherein the particles have an average size of up to about 20 microns, preferably up to about 5 microns, more preferably up to about 2.5 microns. Salts formed from other cations, such as sodium, may also be suitable.

The personal care or personal cleansing compositions containing the inventive ter-polymer may additionally contain further polymers. The further polymer may for example, be:
homopolymer of polyacrylamide of molecular weight ranging from about 1,000,000 to about 30,000,000, about 2,000,000 to about 8,000,000 or about 2,000,000 to about 5,000,000.
a cationic copolymer different than the inventive ter-polymer. For example, the cationic copolymer may be a copolymer of acrylamide and cationic monomers such as
(meth)acryloyloxyethyl-N,N,N-trimethylammonium chloride,
-(meth)acryloyloxyethyl-N-ethyl-N, N-dimethylammonium monoethyl sulfate,
(meth)acryloyloxyethyl-N,N,N-triethylammonium monoethyl sulfate,
-(meth)acryloylaminopropyl-N,N,N-trimethylammonium chloride,
(meth)acryloylaminopropyl-N-ethyl-N,N-dimethylammonium monoethyl sulfate,
(meth)acryloylaminopropyl-N,N-diethyl-N-methylammonium chloride or
(meth)acryloylaminopropyl-N,N-diethyl-N-methylammonium monomethyl sulfate or mixtures thereof.

The second cationic copolymer will typically contain from 0.1 to about 25 weight percent, 4 to about 20 or about 5 or about 20 weight percent cationic monomer based on the total weight of the copolymer.

Preparation of the Ter-Polymer

The amphoteric conditioning polymers can be prepared in the conventional manner, e.g., by mass or solution polymerization. The polymerization may take place in an aqueous, solvent or aqueous-solvent mixed environment but it is preferred that the reaction be carried out in a substantially aqueous environment. Possible solvents are DMSO, THF, DMF, ethyl, propyl, butyl, acetate, benzene, toluene, xylene, N-butanol, isobutanol, isopropanol, MEK, MIBK, acetone, etc.

It is preferred to carry out the polymerization in the absence of oxygen.

The monomers are preferably polymerized using a radical reaction, by addition of peroxides, optionally in the presence of redox systems. Initiators such as ammonium persulfate are ideal as this initiator is highly water soluble.

The polymerization time of the conditioning polymer depends on the temperature and the desired final product properties but is preferably within the range of from 0.5 to 10 hours at temperatures ranging from about 50° C. to about 190° C. The polymerization can be carried out continuously, discontinuously or semicontinuously. If it is preferred to obtain a polymer chain having random distribution of monomers, all of the monomers together will be preferably added to the reaction mixture. This may be done in one portion or metered over time to control the rate of the reaction.

On the basis of the reactivity of the monomers, which is known, a skilled artisan can control the polymerization so as to obtain the desired distribution.

EXAMPLES

Determination of average molecular weight is carried out by gel permeation chromatograph.
Key to Abbreviations
APTAC—acryloylaminopropyl-N,N,N-trimethylammonium chloride
EGDS—ethylene glycol distearate
DAA—diallyamine
ADAA—Alkoxylated Diallyamine—These monomers are prepared according to the examples of U.S. Pat. Nos. 7,579,421 and 5,478,883 herein incorporated entirely by reference
NaEDTA—sodium salt of ethylene diamine tetra acetic acid
Cocamide MEA—Cocamide Monoethanolamine
SLS—Sodium Lauryl Sulfate
SLES-X, Sodium Laureth Sulfate with X moles of ethoxylation
EO/PO—ethoxy/propoxy groups
VA 044—2,2'-Azobis[2-(2-imidazolin-2-yl)propane]dihydrochloride
tBHP—tert butyl hydrogen peroxide
SMBS—Sodium metabisulfite
HLB—hydrophilic-lipophilic balance
Synthesis of Amphoteric Conditioning Polymer Example 1

Preparation of APTAC/AA/DAA Ter-Polymer

| Reactor Charge (RC) | |
|---|---|
| 75% APTAC | 0.7 g |
| 97% DAA | 3.5 g |
| 99% Acrylic Acid | 0.1 g |
| 10% NaEDTA | 1.0 g |
| Deionized Water | 160 g |
| Adjust pH to 4.0 using HCL (5%) solution | |
| Monomer Feed (MF) | |
| 75% APTAC | 114 g |
| 97% DAA | 0.6 g |
| 99% Acrylic Acid | 10 g |
| 0.10% methylenebisacrylamide | 30 g |
| Adjust pH to 4.0 using NaOH solution | |

A one liter reactor is purged with nitrogen. The RC charge is added to the reactor. The reactants are stirred at 210 rpm and heated to 100° C. The intiator (ammonium persulfate, 0.2 g in 20 ml water) is introduced at a rate of 0.22 ml/min while the remaining monomer feeds (MF) is added over a period of 60 min. After the addition of monomer feeds, the container is rinsed with 10 mL DI water. The initiator is fed at the same rate. After the addition of initiator is completed, the batch is held at 100° C. for 0.5 hr. Then Sodium metabisulfite (1 wt % aqueous solution, 2.6 mL) is added at the rate of 0.5 ml/min. The batch is then maintained at 100° C. for another 0.5 hr. The resulting polymer has weight ratios respectively of APTAC/AA/DAA or 86/10/4. MW 210 K Optional Neutralization of the Formed Amphoteric Conditioning Polymer The reactor is cooled to about 60° C. Before discharging the polymer from the reactor a fatty amine or fatty amine oxide is optionally added for example at weight ratios ranging between 0.5:2 to 1:2 (fatty amine to conditioning polymer). The mixture is stirred thoroughly to allow for product homogeneity and neutralization. The fatty amines, fatty amine oxides or fatty quaternary used for neutralization are dodecylamine, dodecyldimethyl amine, dodecyldimethyl amine oxide, myristylamine, myristyldimethyl amine, myristyldimethyl amine oxide, stearylamine, stearyldimethyl amine, stearyldimethyl amine oxide and cetyltrimethyl ammonium Chloride. After neutralization, the polymer is discharged from the reactor The reactor is cooled to about 60° C. Before discharging the polymer from the reactor a dodecylamine is optionally added at weight ratio of 1:2 (fatty amine:conditioning polymer). The mixture is stirred thoroughly to allow for product homogeneity. After neutralization, the polymer is discharged from the reactor.

See Table I for further examples 2-8 containing APTAC:AA:DAA.

Example 9

Preparation of APTAC/AA/AA-alkoxylated Ter-Polymer

|  | Weight, g |
| --- | --- |
| Reactor Charge (RC) | |
| 1. 60% APTAC | 2 |
| 2. DAA -EO/PO 90:10 wt. Ratio[1] | 22.64 |
| 3. Acrylic Acid | 0.2 |
| 4. NaEDTA | 0.2 |
| 5. Citric acid | 1 g |
| 6. HCl (10%) | to adjust pH to 4 |
| 7. Deionized water (DIW) | 250 + 30 (rinse) |
| Monomer feed (MF) | |
| 8. 60% APTAC | 293 |
| 9. Acrylic Acid | 20 |
| 10. MBA (0.1 wt %) | 60 (300 ppm) |
| 11. DI water | 40 + 20 (rinse) |
| Adjust pH to 4 using 1N NaOH | |
| Initiator feed (IF) | |
| 12. tBHP (1 wt %) | 20 g |
| 13. SMBS (1 wt %) | 20 g |
| Post treatment (PT) | |
| 14. VA 044 (200 PPM) | 40 mg |

A terpolymer of 80.6:9.1:10.3 weight ratio of APTAC:AA:DAA-EO/PO is formed.

1. Mw is 1100.

Example 10

|  | Weight, g |
| --- | --- |
| Reactor Charge (RC) | |
| 15. 75% APTAC | 1.4 |
| 16. DAA -EO/PO 80/20[1] | 30 |
| 17. Acrylic Acid | 0.1 |
| 18. NaEDTA | 0.1 |
| 19. Citric acid | 0.5 |
| 20. HCl (10%) | to adjust pH to 4 |
| 21. Deionized water (DIW) | 50 + 20 |
| Monomer feed (MF) | |
| 22. 75% APTAC | 117 |
| 23. Acrylic Acid | 10 |
| 24. MBA (0.1 wt %) | 30 |
| 25. DI water | 50 + 10 |
| Adjust pH to 4 using 1N NaOH | |
| Initiator feed (IF) | |
| 26. tBHP (0.75 wt %) | 20 g |
| 27. SMBS (0.75 wt %) | 20 g |
| Post treatment (PT) | |
| 28. VA 044 (200 PPM) | 40 mg |

A terpolymer of 68.9:7.8:23.3 weight ratio of APTAC:AA:DAA-EO/PO is formed.

1. Mw is 3000.

Procedure

The procedure for examples 2 and 3 are substantially as in example 1 above but a combination of initiators are used (t-BHP and SMBS).

Amphoteric Polymers

Various amphoteric polymers prepared as above in example 1 but ratios of APTAC, Acrylic acid and DAA and all with a Mw of ~210K are varied along with neutralization with different fatty amines.

TABLE 1

Amphoteric polymers formed from APTAC/AA/DAA.

| Example | APTAC (wt. %) | DAA (wt. %) | AA (wt. %) | Amine | X-Link | Mw (×1000) |
| --- | --- | --- | --- | --- | --- | --- |
| 1 | 86 | 4 | 10 | dodecylamine | yes | ~210 |
| 2 | 96 | 4 | 0 | dodecylamine | yes | ~215 |
| 3 | 56 | 4 | 40 | dodecylamine | yes | ~210 |
| 4 | 86 | 4 | 10 | Dodecyldimethyl amino oxide | no | ~210 |
| 5 | 80 | 10 | 10 | NA | no | ~195 |
| 6 | 86 | 4 | 10 | Cetyltrimethyl ammonium Chloride | yes | ~205 |
| 7 | 50 | 10 | 40 | dodecylamine | no | ~215 |
| 8 | 60 | 15 | 25 | NA | No | ~210 |

TABLE 2

| Example | APTAC:AA:DAA (molar ratio) | ADAA (mol %) | ADAA Properties HLB | EO/PO Ratio (MW) | XLink | Mw (×1000) |
|---|---|---|---|---|---|---|
| 9  | 72.9:25.2:0   | 1.9 | 8  | 90/10 (1100)  | Yes | 434 |
| 10 | 72.9:25.2:0   | 1.9 | 17 | 80/20 (3000)  | Yes | 300 |
| 11 | 72.9:25.2:1.9 | 0   | —  | —             | Yes | 728 |
| 12 | 71.7:24.8:1.7 | 1.8 | 17 | 80/20 (3000)  | Yes | 471 |
| 13 | 72.9:25.2:0   | 1.9 | 17 | 80/20 (3000)  | Yes | NA  |
| 14 | 72.9:25.2:0   | 1.9 | 8  | 90/10 (1100)  | Yes | 198 |
| 15 | 72.9:25.2:0   | 1.9 | 9  | 90/10 (1100)  | Yes | 552 |
| 16 | 95.3:0:0      | 4.7 | 17 | 80/20 (3000)  | Yes | 55  |
| 17 | 72.9:25.2:0   | 1.9 | 17 | 80/20 (3000)  | Yes | 223 |
| 19 | 72.9:25.2:0   | 1.9 | 8  | 90/10 (1100)  | Yes | 435 |
| 20 | 42.1:56.5:0   | 1.4 | 17 | 80/20 (3000)  | Yes | 142 |

Personal Cleansing Formulation of the Conditioning Polymer

For the shampoos below, all ingredients are mixed and heated to about 70° C. and homogenized to improve dispersability of silicon and the conditioning ter-polymer/fatty amine complex. Before cooling, NaCl and citric acid are added if necessary to adjust for a viscosity ranging between 7000-8000 cps at room temperature and for a pH of 5.7.

Shampoo 1

| Ingredient | Wt. Percent |
|---|---|
| Sodium Lauryl Ether-2 Sulfate (2 moles of ethoxylation) | 12.00 |
| Coacamidopropyl Betaine | 3.00 |
| EGDS | 2.00 |
| Conditioning Polymer (examples 1-20) | 0.25 (active polymer) |
| Dodecylamine | 0.0 to 0.12% |
| Water | Qs |

Shampoo 2

| Ingredient | Wt. Percent |
|---|---|
| Sodium Lauryl Ether-2 Sulfate (2 moles of ethoxylation) | 12.00 |
| Coacamidopropyl Betaine | 3.00 |
| EGDS | 2.00 |
| Conditioning Polymer (examples 1-20) | 0.25 (active polymer) |
| Lauramine Oxide | 0.0 to 0.12% |
| Water | Qs |

Shampoo 3

| Ingredient | Wt. Percent |
|---|---|
| Ammonium Laureth-3 Sulfate | 10.00 |
| Ammonium Lauryl Sulfate | 4.00 |
| Coacamidopropyl Betaine | 3.00 |
| Cocamide MEA | 1.00 |
| EGDS | 2.00 |
| Conditioning Polymer (examples 1-20) | 0.25 (active polymer) |
| Dodecylamine | 0.0 to 0.12 |
| Water | Qs |

Shampoo 4

| Ingredient | Wt % |
|---|---|
| Sodium Lauryl Ether-2 Sulfate (2 moles of ethoxylation) | 12.00 |
| Cocamidoproyl Betaine | 3.0 |
| Silicone DC-1664 (Dow) | 2.0 |
| EGDS | 2.0 |
| Conditioning Polymer (examples 1-20) | 0.0 to 0.25 (active polymer) |
| Dodecylamine | 0.0 to 0.12 |
| Water | Qs |

Body Wash

| Ingredient | Wt % |
|---|---|
| Sodium Laureth-2 Sulfate | 8.0 |
| Cocamidopropyl Betaine | 2.0 |
| Disodium Laureth Sulfosuccinate | 1.0 |
| PEG-7 Glyceryl Cocoate | 0.5 |
| Conditioning Polymer (examples 1-20) | 0.25 |
| Water | Qs |

| Moisturizing Hand Lotion | |
| --- | --- |
| Ingredient | Wt % |
| Cetostearyl alcohol (50/50) | 5.00 |
| Myristyl Myristate | 5.0 |
| Methyl Glucose Sesquistearate | 0.8 |
| Isopropyl Myristate | 4.0 |
| Conditioning Polymer (examples 1-20) | 0.25 (active polymer) |
| Tween 60 | 2.6 |
| PEG-20 Methyl Glucose | 1.50 |
| White Ceresine Wax | 0.4 |
| Triethanol amine | 0.20 |
| Arlacel 60 | 3.0 |
| Water | Qs |

| Liquid Soap | |
| --- | --- |
| Ingredient | Wt % |
| Sodium laureth sulfate | 10-15.00 |
| Cocamidoproyl Betaine | 15-20 |
| Silicone DC-1664 (Dow) | 2.0 |
| Sunflower Seed Oil | 2.0 |
| Conditioning Polymer (examples 1-20) | 0.25 (active polymer) |
| Sorbitan monolaurate | 1-3 |
| Hydantoin (preservative) | 0.2 |
| Fragrance | 1.0 |
| Styrene Acrylate (opacifier) | 0.4 |
| Water | Qs |

| Shower Gel | |
| --- | --- |
| Ingredient | Wt % |
| Sodium Lauroamphoacetate | 7 |
| Sodium Laureth Sulfate | 14 |
| Cetyl Acetate and Acetylated Lanolin Alcohol | .5 |
| Laurie acid | 2.5-3.0 |
| Sunflower Seed Oil | 3.0 |
| Vitamin E | 1.0 |
| Conditioning Polymer (examples 1-20) | 0.25 (active polymer) |
| Cocamide Monoethanol amide | 2 |
| Guar Hydroxypropyl trimonium chloride | 0.5 |
| Glycerin | 2 |
| Hydantoin (preservative) | 0.2 |
| Fragrance | 1.0 |
| Titanium dioxide | 0.2 |
| Water | Qs |

Application Data

The ter-polymers are formulated into the following shampoo composition for determining their silicone deposition on hair, polymer conditioning effects and reduction in combing energies.

| Ingredient | Wt % |
| --- | --- |
| Sodium Lauryl Ether-2 Sulfate (2 moles of ethoxylation) | 10.00 |
| SLS | 4.0 |
| Cocamide MEA | 1.0 |
| Cocamidoproyl Betaine | 3.0 |
| Sillicone DC-1664 (Dow) | 1.0 |
| EGDS | 2.0 |
| Conditioning Polymer (example 1) | 0.25 (active polymer) |
| Dodecylamine | 0.12 |
| Water | Qs |

Silicone Deposition

Washing Procedure

Ten virgin brown hair tresses are weighed and treated for each shampoo to be tested. Five of the tresses are shampooed twice and five are shampooed ten times. Each tress is pre-washed with 15% TERGITOL rinsed thoroughly and then wet with water.

1 g of shampoo is applied down the length of each tress and lathered. The tresses are rinsed in a flow of tap water (0.4 gallon per minute) for one minute at 35 C. The hair is allowed to dry overnight at room temperature conditions and is then ready for silicone extraction.

Silicone Analysis of Hair

The treated tresses are extracted with 30 ml of a toluene/methylisobutyl ketone (50/50) mixture in glass centrifuge tubes.

Quantitative analysis of silicone is carried out using an atomic absorption analyzer equipped with a graphite furnace (Perkin Elmer AAnalyst 600).

The hair washing analysis and extractions are carried out in triplicate. Furthermore, the hair washing analysis and extractions are repeated two and fourteen days after preparation of the shampoo in order to determine the stability of the shampoos performance upon storage.

Polymer Conditioning Effects

The washing procedure is carried out similarly to washing procedure described above except 9 gram hair tresses, 8 inches long are washed with 2 grams of shampoo. The hair tresses are European brown from International Hair Importers.

The inventive ter-polymers/fatty amine complexes show improved feel and less "squeakiness". The absence or lowering of "squeakiness" is considered an important advantage in 2 and 1 shampoos.

Dry and Wet Combing Energies

Reductions in dry and wet combing energies are measured using a DIASTRON MINIATURE TENSILE TESTER MTTL75.

The wet combing energies are determined by immersing the treated tresses in a beaker of water three times and squeezing out excess water using fingers.

The dry combining energies are determined analogously except the tresses are air dried before measurements.

Table 2

Application Results Containing Various Ter-Polymers

TABLE 3

Results for Ter-Polymers Containing DAA

| Example | Silicon Deposition µg/g | Reduction in combing friction Energy[1] (%) | Reduction in wet friction energy[2] (%) |
| --- | --- | --- | --- |
| Control/No polymer | 26 | 0 | 0 |
| 1 | 389 | 71 | 68 |

TABLE 3-continued

Results for Ter-Polymers Containing DAA

| Example | Silicon Deposition μg/g | Reduction in combing friction Energy[1] (%) | Reduction in wet friction energy[2] (%) |
|---|---|---|---|
| 2 | 432 | 62 | 65 |
| 3 | 394 | 51 | 48 |

[1]Dry hair 9.7% Standard Deviation
[2]Wet hair 10.7% Standard Deviation

TABLE 4

Results for Ter-Polymers Containing Alkoxylated DAA

| Example | Silicon Deposition μg/g | Reduction in combing friction Energy[1] (%) | Reduction in wet friction energy[2] (%) |
|---|---|---|---|
| Control/No polymer | ~26 | 0 | 0 |
| 9 | 398 | 71 | 61 |
| 10 | 243 | 58 | 54 |
| 11 | 432 | 59 | 57 |
| 12 | 378 | 72 | 65 |
| 13 | 343 | 59 | 62 |
| 14 | 168 | 63 | 58 |
| 15 | 412 | 83 | 72 |
| 16 | <12 | 34 | 21 |
| 17 | 173 | 61 | 57 |
| 18 | <12 | 27 | 30 |
| 19 | 411 | 69 | 57 |
| 20 | 146 | 37 | 34 |

[1]Dry hair 11.7% Standard Deviation
[2]Wet hair 10.4% Standard Deviation

The invention claimed is:

1. A conditioning polymer consisting of monomers i), ii) and iii)

wherein monomer -i) is a cationic monomer defined by formula (I)

$$R_1-\underset{H}{\overset{R_2}{C}}=\underset{O}{\overset{}{C}}-X-L-\overset{R_3}{\underset{R_5}{N^+}}-R_4 \quad A^- \quad (I)$$

in which:

$R_1$ and $R_2$ are independently hydrogen or methyl, $R_3$, $R_4$ and $R_5$ are independently linear or branched $C_1$-$C_{30}$ alkyl radicals, X is NH, $NR_6$ or oxygen, $R_6$ is $C_1$-$C_6$ alkyl, L is $C_nH_{2n}$, n is an integer from 1 to 5, and A− is an anion derived from an organic or inorganic acid;

monomer ii) is a monomer of formula (VI):

$$\underset{R_{14}}{\overset{R_{13}}{\diagdown}}C=C\underset{COOM}{\overset{R_{12}}{\diagup}} \quad (VI)$$

$R_{12}$ and $R_{13}$ are independently hydrogen or $C_1$-$C_6$alkyl, $R_{14}$ is hydrogen, $C_1$-$C_6$alkyl or a COOM group, M is hydrogen, a monovalent or divalent metal ion, ammonium or an organic ammonium ion, $R_9$ and $R_{10}$ of the diallyl component iii) are hydrogen and monomer iii) is a diallyl amine monomer defined by formulae (II) or (III)

$$\text{(II)}$$

$$\text{(III)}$$

in which, $R_7$ and $R_8$ are independently hydrogen or $C_1$-$C_4$ alkyl, $R_9$ is hydrogen, branched or linear $C_1$-$C_{30}$ alkyl, $C_1$-$C_{30}$alkoxy, $$*-[AO]_m-R_{11},$$

hydroxy substituted $C_1$-$C_{10}$ alkyl, $C_7$-$C_9$alkylphenyl, carboxyalkyl, alkoxyalkyl and carboxyamidalkyl, $R_{10}$ is hydrogen, $C_1$-$C_{20}$ alkyl, $C_5$-$C_{10}$ cycloalkyl or an unsubstituted benzyl radical, with the proviso that if $R_{10}$ is other than hydrogen, then $R_9$ is $$*-[AO]_m-R_{11},$$

AO is a $C_1$-$C_{12}$ alkylene oxide or mixtures of $C_1$-$C_{12}$ alkylene oxides, m is an integer from 2 to 200, $R_{11}$ is hydrogen or methyl;

and the polymer is optionally crosslinked with a crosslinking agent.

2. The conditioning polymer according to claim 1, wherein the cationic monomer of formula (I) is selected from the group consisting of (meth)acryloyloxyethyl-N,N,N-trimethylammonium chloride, (meth)acryloyloxyethyl-N-ethyl-N,N-dimethylammonium monoethyl sulfate, (meth)acryloyloxyethyl-N,N,N-triethylammonium monoethyl sulfate, (meth)acryloylaminopropyl-N,N,N-trimethylammonium chloride, (meth)acryloylaminopropyl-N-ethyl-N,N-dimethylammonium monoethyl sulfate, (meth)acryloylaminopropyl-N,N-diethyl-N-methylammonium chloride, (meth) acryloylaminopropyl-N,N-diethyl-N-methylammonium monomethyl sulfate and mixture thereof.

3. The conditioning polymer according to claim 1, wherein the monomer of formula (I) makes up about 10 to about 98 weight percent of the formed ter-polymer.

4. The conditioning polymer according to claim 1, wherein the anionic monomer of component ii) makes up about 2 to about 25 weight percent of the total weight of the formed polymer.

5. The conditioning polymer according to claim 1, wherein the diallyl amine monomer of formulae (II) or (III) makes up from 2 to 40 weight percent of the total weight of formed polymer.

6. A conditioning polymer consisting of the monomers i), ii) and iii), wherein the monomer is a cationic monomer defined by formula (I)

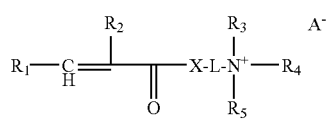

in which:

$R_1$ and $R_2$ are independently hydrogen or methyl, $R_3$, $R_4$ and $R_5$ are independently linear or branched $C_1$-$C_{30}$ alkyl radicals, X is NH, $NR_6$ or oxygen, $R_6$ is $C_1$-$C_6$ alkyl, L is $C_nH_{2n}$, n is an integer from 1 to 5, and A– is an anion derived from an organic or inorganic acid;

monomer ii) is a monomer of formula (VI):

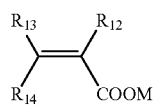

$R_{12}$ and $R_{13}$ are independently hydrogen or $C_1$-$C_6$alkyl, $R_{14}$ is hydrogen, $C_1$-$C_6$alkyl or a COOM group, M is hydrogen, a monovalent or divalent metal ion, ammonium or an organic ammonium ion, $R_9$ and $R_{10}$ of the diallyl component iii) are hydrogen; and monomer iii) is a diallyl amine monomer defined by formulae (IIa) or (IIIa)

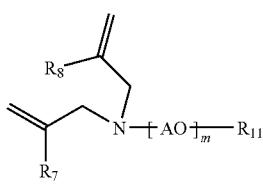

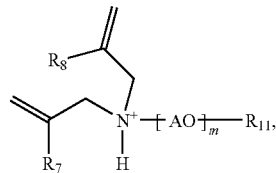

AO is a $C_1$-$C_{12}$ alkylene oxide or mixtures of $C_1$-$C_{12}$ alkylene oxides, m is an integer from 2 to 200, and $R_{11}$ is hydrogen or methyl and the polymer is optionally crosslinked with a crosslinking agent.

7. The conditioning polymer according to claim 6, wherein the average molecular weight of the monomer of (IIa) and (IIIa) varies from about 500 to about 3500.

8. The conditioning polymer according to claim 6, wherein the hydrophilic-lipophilic balance of the monomer of formula (IIa) or (IIIa) is between about 5 to about 18.

9. The conditioning polymer according to claim 6, wherein the monomer of formula (IIa) or (IIIa) is formed by the reaction of diallyamine with about 10 to about 30 wt. percent propylene oxide and about 90 to about 70 wt. percent ethylene oxide, wherein the wt. percent is based on the total weight of the monomer of formula (IIa) or (IIIa).

10. The conditioning polymer according to claim 1, wherein the conditioning polymer has an average molecular weight of about 10,000 to about 18,000,000.

11. A personal cleansing or personal care composition comprising the conditioning polymer according to claim 1, wherein the conditioning polymer is dispersed or solublilized in a cosmetically acceptable vehicle.

12. The personal cleaning composition according to claim 11 further comprising a fatty amine

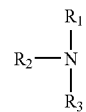

wherein $R_1$ is a $C_8$-$C_{30}$ straight or branched chain aliphatic, $R_2$ and $R_3$ are independently hydrogen, $C_1$-$C_{30}$ straight or branched chain aliphatic;

or a fatty amine oxide

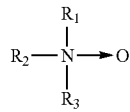

wherein $R_1$ contains an alkyl, alkenyl or monohydroxy alkyl radical of from 8 to about 18 carbon atoms, from 0 to about 10 ethylene oxide moieties, and from 0 to about 1 glyceryl moiety, and $R_2$ and $R_3$ contain from 1 to about 3 carbon atoms and from 0 to 1 hydroxy group.

13. The conditioning polymer according to claim 12, wherein the weight ratio of the conditioning polymer and fatty amine, fatty amine oxide or fatty quaternary ranges from about 1:5 to about 5:1.

14. The personal cleansing or personal care composition according to claim 11 which further comprises at last one surfactant chosen from anionic, amphoteric, nonionic and zwitterionic surfactants.

15. The personal cleansing or personal care composition according to claim 11, wherein the personal cleansing composition is a shampoo or bodywash.

16. The personal cleansing composition according to claim 11, wherein the cleansing composition is a 2-in-1 shampoo, a bodywash, a facial wash, a bubble bath, soapless cleansers, liquid soap, bar soap; a shower gel, xfoliating shower gel; a milk bath; moist towelletes; bath effervescent tablets; bubble bath; a bath gel; shower gel or a shower cream and further comprises a detersive anionic surfactant from about 5% to about 50% by weight of the composition.

17. The personal care composition according to claim 11, wherein the personal care composition is a hand lotion, body lotion, a body spray, gel, hair conditioning rinse, shaving cream, foam, soap, an after-shave, after-shave moisturizer, a hand cream nail cream or a depilatory cream.

18. A process for conditioning a keratinous substrate comprising the steps of applying an effective amount of a composition comprising the conditioning polymer according to claim 1 to the keratinous substrate.

19. The process according to claim 18, wherein the keratinous substrate is human or animal skin, hair or nails.

20. A method for enhancing the deposition of silicone to skin, hair or nails comprising the steps of
topically applying a composition comprising
  i) the conditioning polymer according to claim 1,
  ii) at least one silicone compound
and
optionally,
  iii) an effective amount of a benefit agent to a desired location on the skin, hair or nails.

21. A personal cleansing or personal care composition comprising the conditioning polymer according to claim 1 and a second polymer selected from the group of polymers consisting of homopolymers of acrylamide, and copolymers of acrylamide and a cationic monomer, wherein the cationic monomer is selected from the group consisting of (meth)acryloyloxyethyl-N,N,N-trimethylammonium chloride, -(meth)acryloyloxyethyl-N-ethyl-N,N-dimethylammonium monoethyl sulfate, (meth)acryloyloxyethyl-N,N,N-triethylammonium monoethyl sulfate, -(meth)acryloylaminopropyl-N,N,N-trimethylammonium chloride, (meth)acryloylaminopropyl-N-ethyl-N,N-dimethylammonium monoethyl sulfate, (meth)acryloylaminopropyl-N,N-diethyl-N-methylammonium chloride, (meth)acryloylaminopropyl-N,N-diethyl-N-methylammonium monomethyl sulfate and mixtures thereof and the second polymer is different than the conditioning polymer.

22. The personal cleansing composition according to claim 16, wherein the cleansing composition is a 2-in-1 shampoo further comprises a detersive anionic surfactant from about 5% to about 50%.

* * * * *